(12) United States Patent
Murakoshi et al.

(10) Patent No.: US 8,184,771 B2
(45) Date of Patent: May 22, 2012

(54) RADIATION PHASE CONTRAST IMAGING APPARATUS

(75) Inventors: Dai Murakoshi, Kanagawa-ken (JP); Kenji Takahashi, Kanagawa-ken (JP)

(73) Assignee: Fujifilm Corporation (JP)

( * ) Notice: Subject to any disclaimer, the term of this patent is extended or adjusted under 35 U.S.C. 154(b) by 157 days.

(21) Appl. No.: 12/748,770

(22) Filed: Mar. 29, 2010

(65) Prior Publication Data

US 2010/0246765 A1 Sep. 30, 2010

(30) Foreign Application Priority Data

Mar. 31, 2009 (JP) .................................. 2009-084385

(51) Int. Cl.
*G01N 23/04* (2006.01)
(52) U.S. Cl. .......................................... 378/62; 378/145
(58) Field of Classification Search .................... 378/36, 378/62, 84, 85, 145, 146
See application file for complete search history.

(56) References Cited

U.S. PATENT DOCUMENTS

| | | | | |
|---|---|---|---|---|
| 3,962,579 A | * | 6/1976 | Winnek | 378/41 |
| 7,180,979 B2 | | 2/2007 | Momose | |
| 2010/0080341 A1 | * | 4/2010 | Popescu et al. | 378/19 |
| 2010/0272230 A1 | * | 10/2010 | Koehler | 378/36 |

OTHER PUBLICATIONS

F. Pfeiffer et al.; "Phase retrieval and differential phase-contrast imaging with low-brillance X-ray sources"; Nature Physics 2; pp. 258-261; 2006.
K. Stetson et al.; "Electrooptic holography and its application to hologram interferometry"; Applied Optics; vol. 21; pp. 3631-3637; 1985.

* cited by examiner

*Primary Examiner* — Hoon Song
(74) *Attorney, Agent, or Firm* — Studebaker & Brackett PC; Donald R. Studebaker

(57) ABSTRACT

A radiation phase contrast imaging apparatus, including a radiation emission unit having a plurality of electron sources for emitting electron beams, and a target for emitting radiation through collision of electron beam emitted from each electron source, a first grating in which grating structures for diffracting radiation are disposed periodically, a second grating in which grating structures for transmitting and shielding radiation are disposed periodically, and a radiation image detector for detecting radiation transmitted through the second grating, in which the first and second gratings are disposed in an optical axis direction of the radiation so as to be able to substantially superimpose each image of the first grating formed based on radiation corresponding to each electron source on a surface of the second grating, and the radiation corresponding to each electron source forms each phase image of the same subject on the radiation image detector.

18 Claims, 20 Drawing Sheets

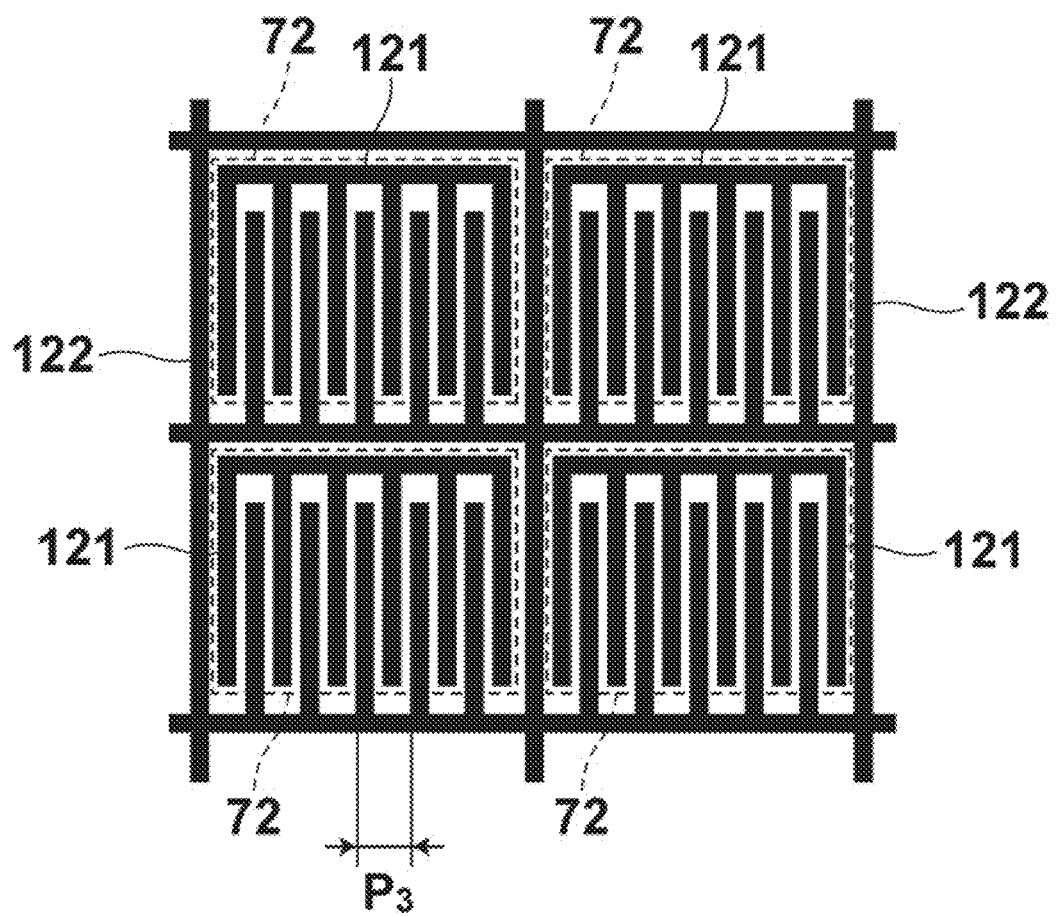

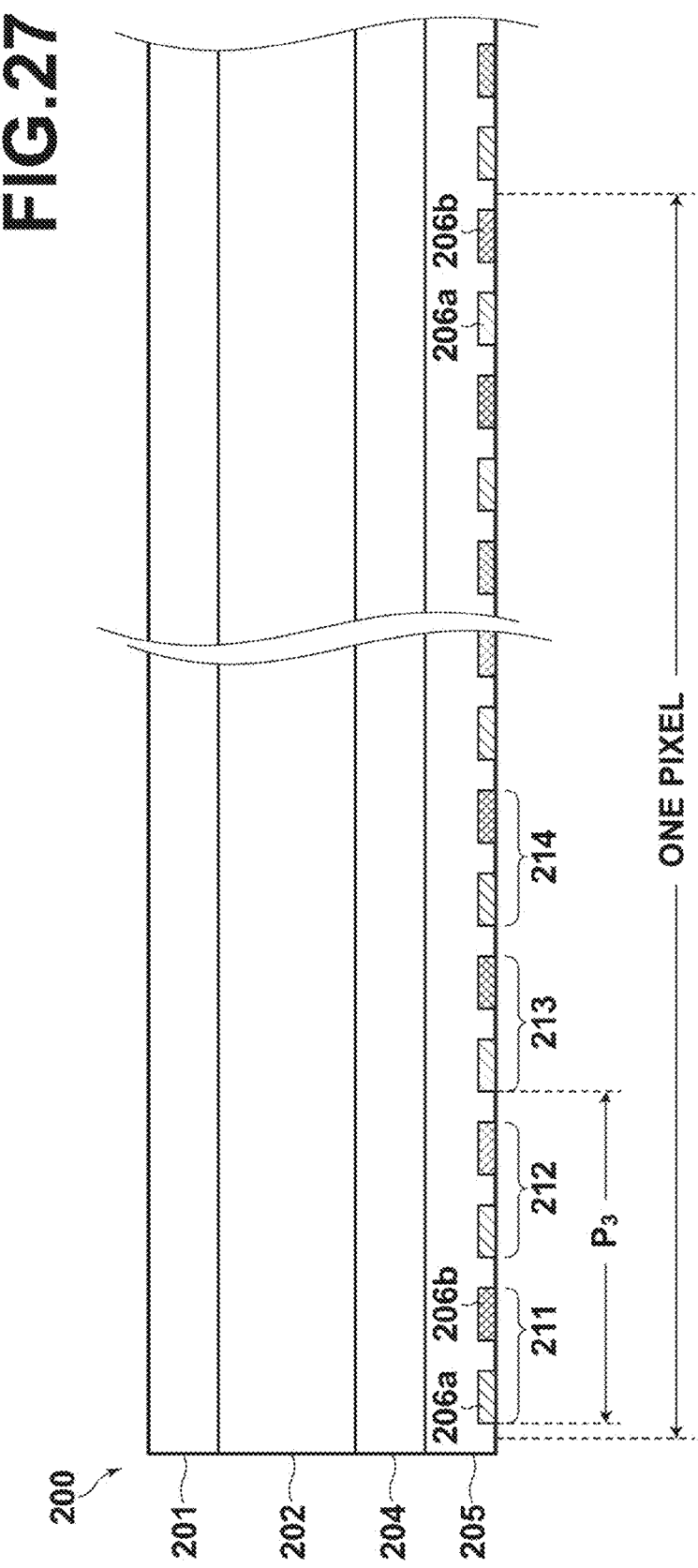

RADIATION PHASE CONTRAST IMAGING APPARATUS

BACKGROUND OF THE INVENTION

1. Field of the Invention

The present invention relates to a radiation phase contrast imaging apparatus using a grating.

2. Description of the Related Art

A method for detecting a variation of wavefront arising from a difference in refractive index of media in a transmission path of an X-ray incident on a subject using an X-ray Talbot interferometer to generate an image of the subject is proposed as described, for example, in U.S. Pat. No. 7,180,979.

The method described above has a potentiality to utilize a corn beam X-ray source or the like, as opposed to other phase imaging methods that uses a crystal analysis body which basically requires parallel monochrome X-rays.

The method using a Talbot interferometer uses, for example, a microfocus X-ray source because it requires a high degree of spatial coherence. Such an X-ray source can yield quite a small amount of X-rays in a short exposure time of several seconds, so it necessitates a longer time of X-ray exposure in comparison with a conventional radiography technique. Thus, the method poses a problem that a favorable phase image can not be obtained due to mechanical instability, body movement of the subject, or the like during the exposure period for detecting a subtle variation of the wavefront.

Consequently, in order to solve the problem, a method that uses a Talbot-Lau interferometer, which is a modification of the method using a Talbot interferometer, is proposed as described, for example, in F. Pfeiffer et al., "Phase retrieval and differential phase-contrast imaging with low-brilliance X-ray sources", Nature Physics 2, pp. 258-261, 2006. The method secures a sufficient X-ray yield in a short time by disposing a multi-slit unit just after the focus of a relatively large focus X-ray source to form a new array of microfocus X-ray sources with each slit as an independent radiation point.

In the method using a Talbot-Lau interferometer, however, it is necessary to make the focus size of the X-ray source sufficiently small relative to the pitch of the first grating in order to ensure a high degree of spatial coherence. Consequently, it is necessary to form a very small slit using a member having a low X-ray transmittance, and it has been very difficult to manufacture such multi-slit units.

When a Talbot-Lau interferometer is configured by disposing a first grating and a second grating from the X-ray source side, the multi-slit unit and gratings need to have high dimensional accuracy and each optical element needs to be geometrically arranged highly accurately.

In view of the circumstances described above, it is an object of the present invention to provide a radiation phase contrast imaging apparatus capable of acquiring a radiation phase contrast image without using a multi-slit unit like that described above.

It is a further object of the present invention to provide a radiation phase contrast imaging apparatus capable of acquiring a radiation phase contrast image without requiring highly precise gratings and geometrical arrangement of each optical element.

SUMMARY OF THE INVENTION

A first radiation phase contrast imaging apparatus of the present invention is an apparatus, including: a radiation emission unit having a plurality of electron sources, each for emitting an electron beam, and a target for emitting radiation through collision of the electron beam emitted from each electron source; a first grating in which grating structures for diffracting radiation emitted from the radiation emission unit are disposed periodically; a second grating in which grating structures for transmitting and shielding radiation diffracted by the first grating are disposed periodically; and a radiation image detector for detecting radiation transmitted through the second grating, wherein: the first and second gratings are disposed in an optical axis direction of the radiation so as to be able to substantially superimpose each image of the first grating formed based on radiation corresponding to each electron source on a surface of the second grating; and the radiation corresponding to each electron source forms each phase image of the same subject on the radiation image detector by way of the first and second gratings.

The first radiation phase contrast imaging apparatus described above may be configured such that an interval $P_0$ between the center of each focus of the radiation corresponding to each electron source, a distance $L_1$ between the focus and the first grating, a distance $Z_1$ between the first grating and the second grating, and a periodic interval $P_2$ between shielding members constituting the second grating and disposed periodically satisfy Formula (1) below.

$$P_0 = P_2 \times L_1 / Z_1 \tag{1}$$

Further, an interval between the center of each focus of the radiation corresponding to each electron source in a direction orthogonal to an extending direction of shielding members constituting the first grating may be 10 to 500 μm.

Still further, the first radiation phase contrast imaging apparatus may further include an electron beam emission control unit for independently controlling the emission of electron beam from each of the plurality of electron sources to the target.

The electron beam emission control unit may be a unit that controls the emission of electron beam to the target by switching a voltage applied to a gate electrode provided between the electron sources and the target and restricts the passage of the electron beam.

Further, the electron beam emission control unit may be a unit that controls the emission of electron beam to the target by switching a potential difference between an extraction electrode, which is provided between the electron sources and the target, and each electron source.

Still further, the electron beam emission control unit may be a unit that controls a focus interval of the radiation by independently controlling the emission of electron beam from each of the plurality of electron sources to the target.

Further, the electron beam emission control unit may be a unit that controls the focus interval of the radiation such that the contrast of a moiré fringe pattern in a radiation image detected by the radiation image detector without a subject being present becomes maximum.

The first grating may be a phase modulation grating and the second grating may be an amplitude modulation grating.

Further, the first and second gratings may be amplitude modulation gratings.

A second radiation phase contrast imaging apparatus of the present invention is an apparatus, including: a radiation emission unit having a plurality of electron sources, each for emitting an electron beam, and a target for emitting radiation through collision of the electron beam emitted from each electron source; a grating in which grating structures for diffracting radiation emitted from the radiation emission unit are disposed periodically; and a periodic information imaging radiation image detector for detecting periodic information of radiation diffracted by the grating, wherein: the grating and the periodic information imaging radiation image detector are disposed in an optical axis direction of the radiation so as to be able to substantially superimpose each image of the grating formed based on radiation corresponding to each electron source on a surface of the periodic information imaging radiation image detector; and the radiation corresponding to each electron source forms each phase image of the same subject inside of the periodic information imaging radiation image detector by way of the grating and linear electrodes of the periodic information imaging radiation image detector.

The second radiation phase contrast imaging apparatus may be configured such that an interval $P_0$ between the center of each focus of the radiation corresponding to each electron source, a distance $L_2$ between the focus and the grating, a distance $Z_2$ between the grating and the periodic information imaging radiation image detector, and an interval $P_3$ between the linear electrodes constituting the periodic information imaging radiation image detector satisfy Formula (2) below.

$$P_0 = P_3 \times L_2 / Z_2 \tag{2}$$

Further, an interval between the center of each focus of the radiation corresponding to each electron source in a direction orthogonal to an extending direction of shielding members constituting the grating may be 10 to 500 μm.

Still further, the second radiation phase contrast imaging apparatus may further include an electron beam emission control unit for independently controlling the emission of electron beam from each of the plurality of electron sources to the target.

The electron beam emission control unit may be a unit that controls the emission of electron beam to the target by switching a voltage applied to a gate electrode provided between the electron sources and the target and restricts the passage of the electron beam.

Further, the electron beam emission control unit may be a unit that controls the emission of electron beam to the target by switching a potential difference between an extraction electrode, which is provided between the electron sources and the target, and each electron source.

Still further, the electron beam emission control unit may be a unit that controls a focus interval of the radiation by independently controlling the emission of electron beam from each of the plurality of electron sources to the target.

Further, the electron beam emission control unit may be a unit that controls the focus interval of the radiation such that the contrast of a moiré fringe pattern in a radiation image detected by the periodic information imaging radiation image detector without a subject being present becomes maximum.

According to the first radiation phase contrast imaging apparatus of the present invention, a plurality of electron sources, each for emitting an electron beam, is provided, and first and second gratings are disposed so as to be able to substantially superimpose each image of the first grating formed based on radiation corresponding to each electron source on a surface of the second grating and each phase image of the same subject is formed on the radiation image detector by the radiation corresponding to each electron source by way of the first grating and second grating.

Further, when an electron beam emission control unit is further provided for independently controlling the emission of electron beam from each of the plurality of electron sources to the target, the focus interval of the radiation may be changed/set such that a grating image formed by radiation from each focus by way of the first grating is substantially superimposed with the structure of the second grating by controlling, after installing the radiation sources, first grating, and second grating, the emission of electron beam emitted from each electron source to the target. This allows a radiation phase contrast imaging apparatus to be configured without requiring highly precise gratings and geometrical arrangement of each optical element.

Still further, when a gate electrode that restricts the passage of the electron beam is provided between the electron sources and the target and the emission of the electron beam to the target is controlled by switching a voltage applied to the gate electrode by the electron beam emission control unit, or the emission of the electron beam to the target is controlled by controlling a potential difference between an extraction electrode, which is provided between the electron sources and the target, and each electron source by the electron beam emission control unit, the focus position of radiation may be changed by a simple structure.

Further, if the electron beam emission control unit is a unit that controls the focus interval of the radiation such that the contrast of a moiré fringe pattern in a radiation image detected by the radiation image detector without a subject being present becomes maximum, the focus interval of radiation may be set automatically, and more appropriate phase images may be obtained.

According to the second radiation phase contrast imaging apparatus of the present invention, a plurality of electron sources, each for emitting an electron beam, is provided, then the grating and the periodic information imaging radiation image detector are disposed in an optical axis direction of the radiation so as to be able to substantially superimpose each image of the grating formed based on radiation corresponding to each electron source on a surface of the periodic information imaging radiation image detector, and each phase image of the same subject is formed inside of the periodic information imaging radiation image detector by the radiation corresponding to each electron source by way of the grating and linear electrodes of the periodic information imaging radiation image detector. This allows a radiation phase contrast imaging apparatus to be formed without using a multi-slit unit, as in the first radiation phase contrast imaging apparatus of the present invention. Further, the use of the periodic information imaging radiation image detector allows the apparatus to be formed with only one grating, whereby the cost of the apparatus may be reduced.

BRIEF DESCRIPTION OF THE DRAWINGS

FIG. 25 illustrates a modification of the periodic information imaging radiation image detector of the radiation phase contrast imaging apparatus according to the second embodiment.

FIG. 27 illustrates a structure of linear electrodes of periodic information imaging radiation image detector in the third embodiment of the radiation phase contrast imaging apparatus of the present invention.

DESCRIPTION OF THE PREFERRED EMBODIMENTS

Figure 1:
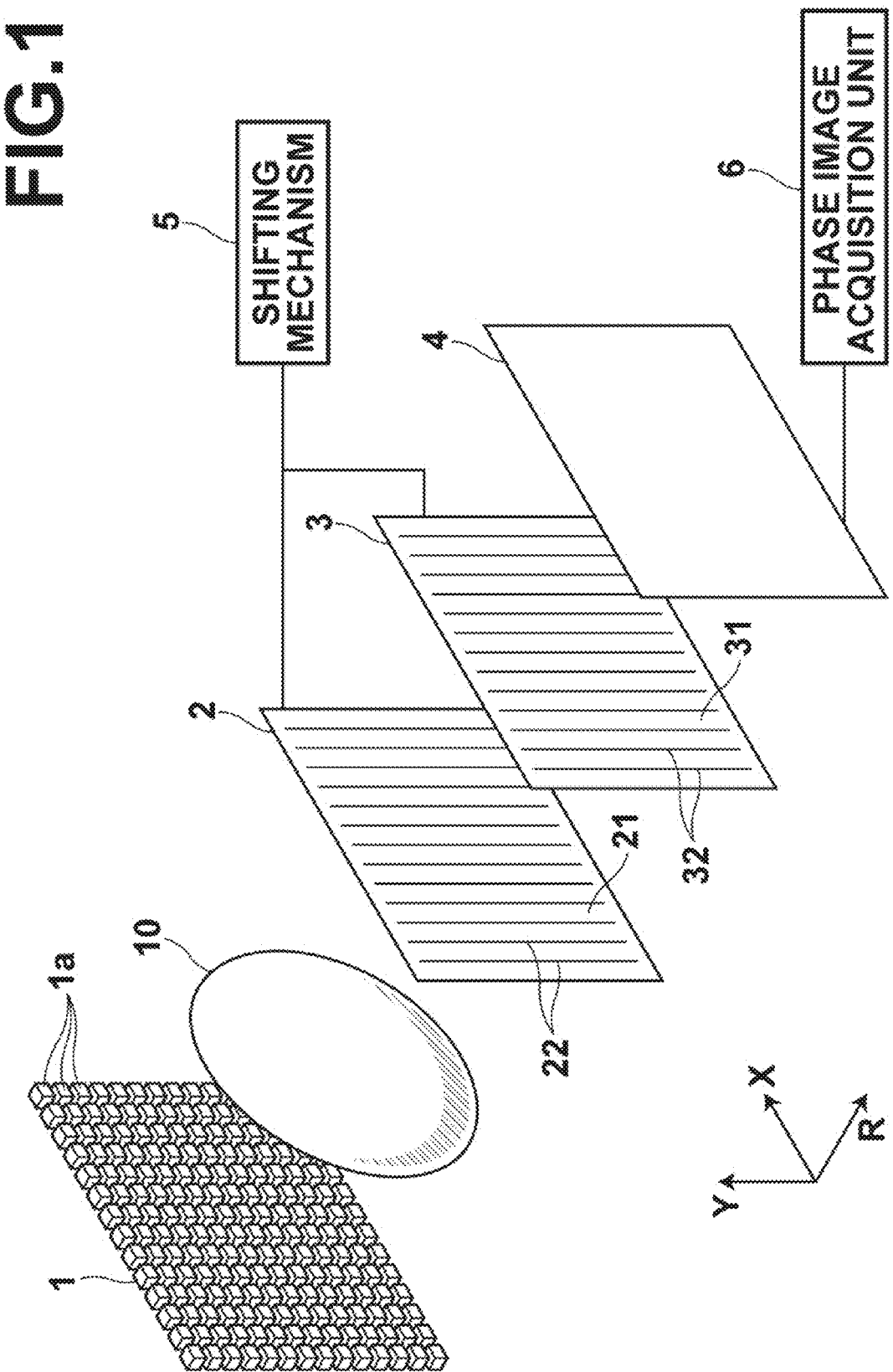
FIG. 1 is a schematic construction diagram of a first embodiment of the radiation phase contrast imaging apparatus of the present invention.
Figure 2:
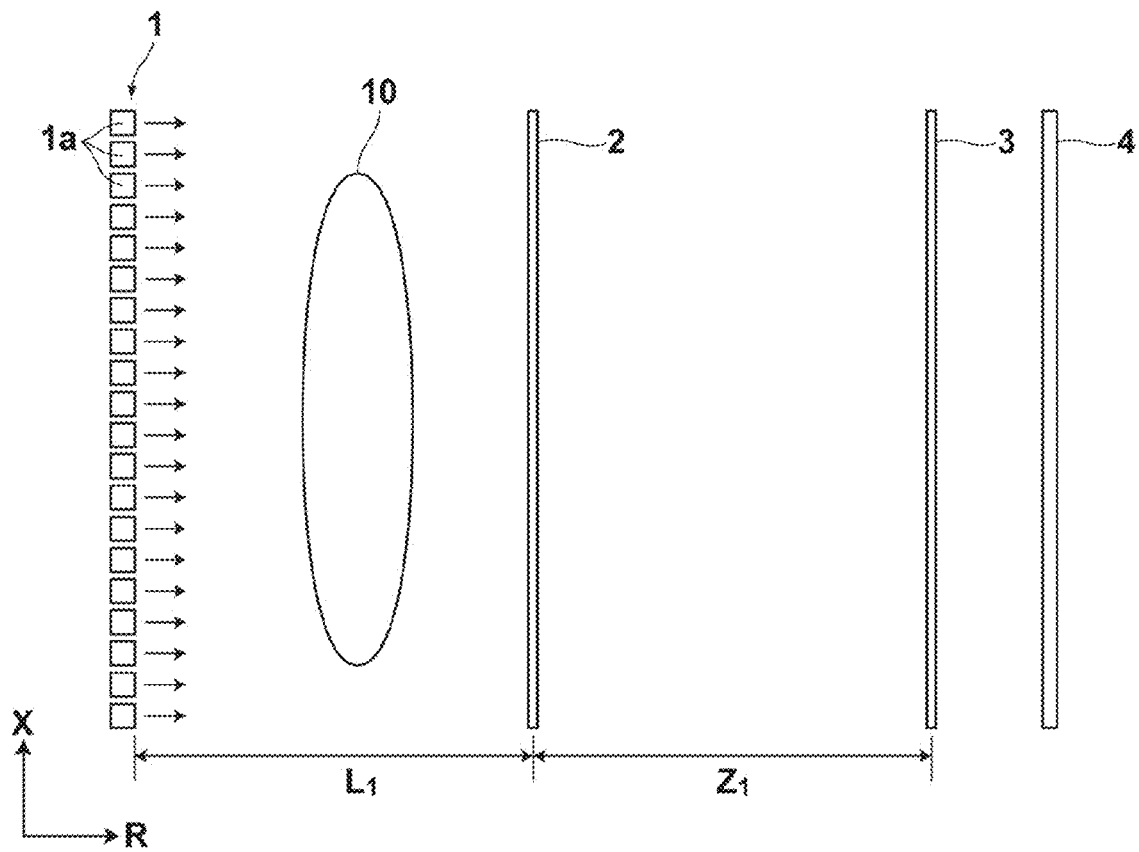
FIG. 2 is a top view of the radiation phase contrast imaging apparatus shown in FIG. 1.

Hereinafter, a first embodiment of the radiation phase contrast imaging apparatus of the present invention will be described with reference to the accompanying drawings. A schematic construction of the radiation phase contrast imaging apparatus according to the first embodiment is shown in FIG. 1. FIG. 2 is a top view (X-R cross-section) of the radiation phase contrast imaging apparatus shown in FIG. 1. The thickness direction in FIG. 2 corresponds to Y direction in FIG. 1.

As illustrated in FIG. 1, the radiation phase contrast imaging apparatus includes radiation emission unit 1 for emitting radiation onto subject 10, first diffraction grating 2 for receiving radiation transmitted through subject 10 and diffracting the radiation, second diffraction grating 3 for transmitting and shielding the radiation diffracted by first diffraction grating 2, radiation image detector 4 for detecting the radiation transmitted through second diffraction grating 3, shifting mechanism 5 for shifting first diffraction grating 2 and second diffraction grating 3 in a direction orthogonal to diffraction members (X direction in FIG. 1) along the respective planes, and phase image acquisition unit 6 for forming a phase image based on an image signal detected by radiation image detector 4.

Figure 3:
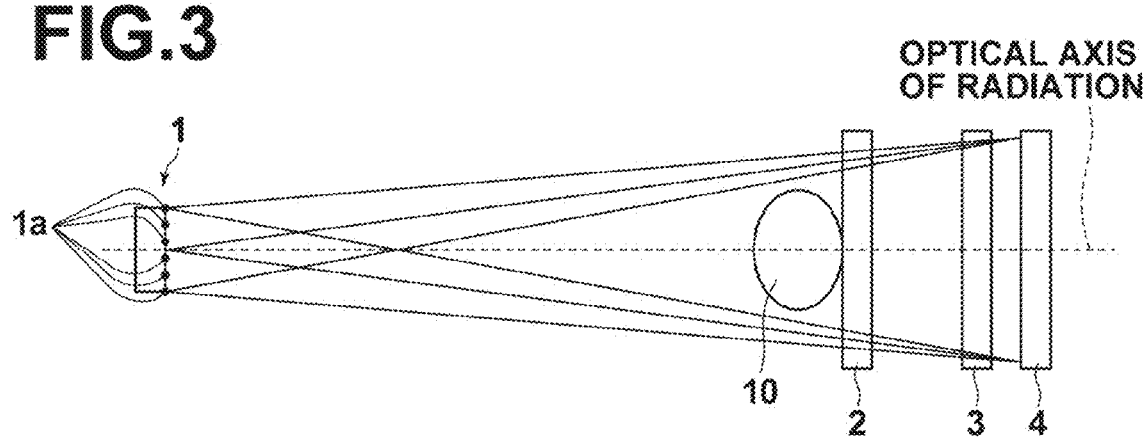
FIG. 3 illustrates a radiation ray emitted from each radiation source.

As shown in FIG. 1, radiation emission unit 1 includes multiple radiation sources 1a, each for emitting radiation, disposed two-dimensionally along a planar surface. The radiation emitted from each radiation source 1a is detected by radiation image detector 4 after transmitting through a subject. The radiation emitted from each radiation source 1a propagates as a spherical wave and receives interactions, such as absorption, scattering, and diffraction in the subject. Each radiation bundle emitted from each radiation source 1a and transmitted through the subject forms a grating image of the first grating at the position of the second grating. Here, by disposing each radiation source 1a, first grating 2, and second grating 3 at predetermined distances in the optical axis direction of the radiation, each radiation bundle overlaps with each other displaced in X direction by an integer multiple of the pitch of the first grating. This may, therefore, increase the signal intensity by a plurality of radiation bundles, but not increase a geometrical blur induced by radiation emitting area enhancement, whereby Exposure time may be reduced. Note that, in FIG. 2, the radiation emitted from each radiation source 1a is schematically indicated simply by an arrow but in actuality, the radiation emitted from each radiation source 1a is radially extended and covers the entirety of the subject, as shown in FIG. 3.

Figure 4:
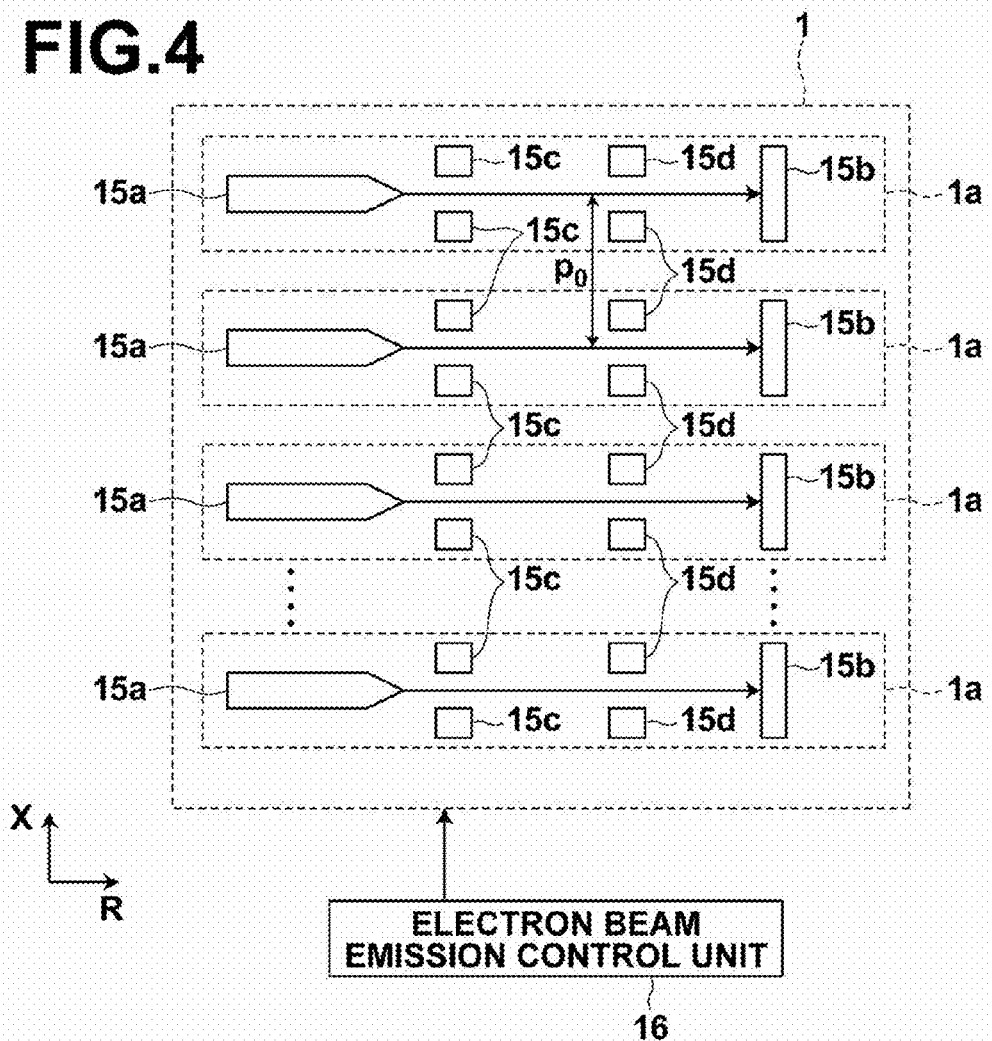
FIG. 4 is a schematic construction diagram of a radiation source.

FIG. 4 shows a schematic construction of each radiation source 1a. As shown in FIG. 4, radiation source 1a includes electron source 15a that emits an electron beam, target 15b that emits radiation through the collision of the electron beam emitted from electron source 15a, extraction electrode 15c that cause electron source 15a to emit an electron beam and accelerate the electron beam, and electrostatic lense 15d that focus the electron beam emitted from the electron source 15a toward the target 15b.

Electron source 15a is formed, as a cathode, of, for example, a carbon nanotube.

Target 15b is formed, as an anode, of a metal material, such as tungsten, molybdenum, copper, or the like.

A high voltage source (not shown) for applying a high voltage is provided between extraction electrode 15c and target 15b, and a voltage for forming a potential difference that accelerates electrons from extraction electrode 15c toward target 15b is applied by the high voltage source.

A voltage source (not shown) is provided between electron source 15a and extraction electrode 15c that provides a potential difference for extracting electrons from electron source 15a toward extraction electrode 15c.

When voltages are applied between electron source 15a and extraction electrode 15c and between extraction electrode 15c and target 15b respectively, an electron beam is emitted from electron source 15a.

Electrostatic lenses 15d form an electric field when a predetermined voltage is applied, and the electron beam emitted from the electron source 15a is focused on target 15b by the electric field.

As shown in FIG. 4, multiple radiation sources 1a are disposed such that the interval between the center of each focus of radiation generated through the collision of the electron beam emitted from each radiation source becomes $P_0$. The interval between the centers of radiation focuses, that is, the interval $P_0$ between the center of each focus of radiation of the present embodiment is set to, for example, 10 to 500 µm, and preferably set to 50 to 200 µm. This interval is determined based on the distance from the focus to first grating 2 and the distance from the focus to second grating 3, the detail of which will be described later.

Radiation source 15a is a source having electron source 15a, target 15b, extraction electrode 15c, and electrostatic lens 15d disposed in a vacuum housing.

Radiation emission unit 1 further includes electron beam emission control unit 16, as shown in FIG. 4. Electron beam emission control unit 16 controls the emission of electron beams emitted from a plurality of electron sources 15a onto target 15b independently from each other. In the present embodiment, electron beam emission control unit 16 controls the emission of an electron beam from each electron source 15a independently of each other by independently controlling the high voltage applied between each extraction electrode 15c and each target 15b with respect to each extraction electrode 15c.

Figure 5:
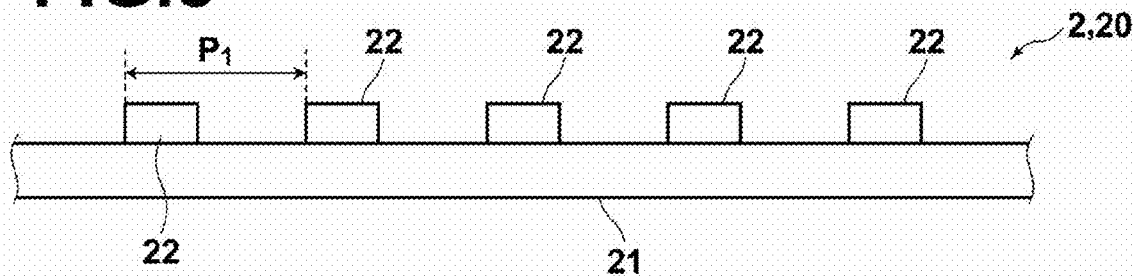
FIG. 5 is a schematic construction diagram of a first grating.

First grating 2 is formed along a surface parallel to the surface on which multiple radiation sources 1a are disposed. As shown in FIG. 5, first grating 2 includes substrate 21 and a plurality of members 22 provided on substrate 21. Each of the plurality of members 22 is formed in a linear shape extending in one direction (thickness direction in FIG. 5). Spacing $P_1$ between each of the plurality of members 22 (the period of the grating) is constant in the present embodiment. As for the material of member 22, for example, gold or silicon may be used. Preferably, member 22 forms a so-called phase modulation grating that gives a phase modulation of about 90° or about 180° to the emitted radiation. The thickness of gold required in the X-ray energy range of ordinary medical diagnosis is, for example, about one to several micrometers. An amplitude modulation grating may also be used. In this case, member 22 needs to have a thickness which is thick enough to sufficiently absorb radiation. For example, the thickness of gold required in the X-ray energy range of ordinary medical diagnosis, in this case, is about ten to several tens of micrometers.

Figure 6:
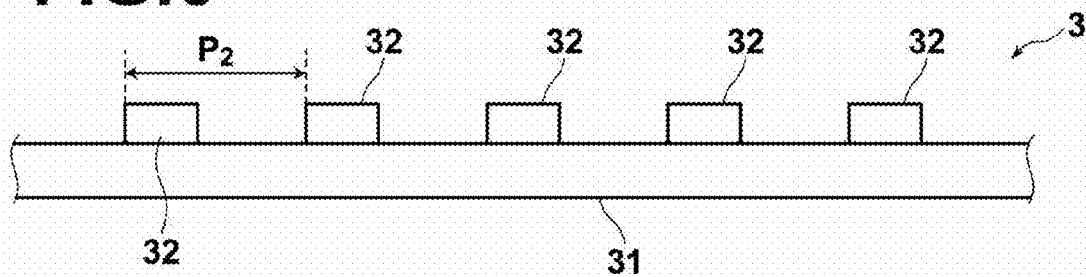
FIG. 6 is a schematic construction diagram of a second grating.

Second grating 3 is formed along a surface parallel to the surface on which multiple radiation sources 1a are disposed. As shown in FIG. 6, second diffraction grating 3 includes substrate 31 and a plurality of members 32 provided on substrate 31, as in first grating 2. Each of the plurality of members 32 is formed in a linear shape extending in one direction (thickness direction in FIG. 6). Spacing $P_2$ between each of the plurality of members 32 (the period of the grating) is constant in the present embodiment. As for the material of member 32, for example, gold may be used. Preferably, second grating 3 is an amplitude modulation grating having thicker members 32. Member 32 needs to have a thickness which is thick enough to sufficiently absorb radiation. For example, the thickness of gold required in the X-ray energy range of ordinary medical diagnosis is about ten to several tens of micrometers.

Here, in the present embodiment, the focus of the radiation corresponding to each electron source 15a of radiation source 1a, first grating 2, and second grating 3 are disposed at predetermined distances in the optical axis direction of the radiation.

More specifically, the radiation phase contrast imaging apparatus of the present embodiment is configured such that an interval $P_0$ between the center of each focus of radiation corresponding to each electron source 15a, a distance $L_1$ (FIG. 2) between the focus and first grating 2, a distance $Z_1$ (FIG. 2) between first grating 2 and second grating 3, and an interval $P_2$ (FIG. 6) between members constituting second grating 3 satisfy Formula (1) below.

$$P_0 = P_2 \times L_1 / Z_1 \qquad (1)$$

With respect to the interval $P_0$ between each focus of radiation corresponding to each electron source 15a, it is possible to dispose each electron source 15a in advance at an interval that satisfies Formula (1) above, or the interval may be adjusted to $P_0$ by outputting electron beams from only a certain electron source 15a through control of electron beam emission control unit 16.

Even when each electron source 15a is disposed, in advance, at an appropriate interval $P_0$ that satisfies Formula (1) above, it often may be displaced from the desired position because of various causes of system perturbation, e.g., a device manufacturing error from design interval $P_0$, a geometrical displacement over time. In such a case, the interval may be adjusted to $P_0$ by emitting electron beams from only some of the all of electron sources 15a through control of electron beam emission control unit 16. The method for selecting a certain electron source 15a, when emitting electron beams from only a certain electron source 15a, will be described later.

Radiation image detector 4 is a detector that detects a self-image of first grating 2 formed by radiation incident on first grating 2 as an image signal intensity modulated by second grating 3. As for radiation image detector 4, detectors used in conventional radiation phase contrast imaging apparatuses, such as direct conversion or indirect conversion flat panel detectors, imaging plates, intensifying screen-film combinations, and the like. Therefore, it will not be elaborated upon further here.

A radiation phase contrast imaging apparatus capable of obtaining a radiation phase image is configured by radiation source 1a, first grating 2, second grating 3, and radiation image detector 4. But, in order to make this configuration function as a Talbot interferometer, the configuration must further substantially satisfy several conditions, which will be described hereinafter.

The distance $Z_1$ between first grating 2 and second grating 3 must substantially satisfy the condition below when first grating 2 is a phase modulation grating that gives a phase modulation of 90°.

$$Z_1 = \left(m + \frac{1}{2}\right)\frac{P_1^2}{\lambda} \quad (2)$$

where, $\lambda$ is the wavelength of radiation (normally, center wavelength), m is 0 or a positive integer, and $P_1$ is the grating pitch of first grating 2.

Further, the distance $Z_1$ must substantially satisfy the condition below when first grating 2 is a phase modulation grating that gives a phase modulation of 180° or an amplitude modulation grating.

$$Z_1 = (m+1)\frac{P_1^2}{\lambda} \quad (3)$$

As described above, shifting mechanism 5 is a mechanism for shifting first and second gratings 2, 3 in X direction. For example, first and second gratings 2, 3 may be shifted by 1/n (n is an integer not less than 2) of the grating pitch $P_2$ of second grating 3 and take a radiation image at each position, whereby n types of n image signals may be obtained. From the n types of image signals, the amount of differential phase shift with respect to each pixel, that is, an amount corresponding to a diffraction angle of radiation caused by subject 10 may be restored, for example, by the fringe scanning method described in K. A. Stetson and W. R. Brohinsky, "Electrooptic holography and its application to hologram interferometry", Applied Optics, Vol. 24, No. 21, pp. 3631-3637, 1985, which may be provided as a so-called phase contrast image through various types of image processing and representations.

An operation of the radiation phase contrast imaging apparatus of the present embodiment will now be described.

First, as illustrated in FIG. 1, subject 10 is placed between radiation emission unit 1 and first grating 2. Then, in each radiation source 1a of radiation emission unit 1, a voltage is applied between electron source 15a and extraction electrode 15c, and a high voltage is applied between extraction electrode 15c and target 15b, which causes an electron beam to be emitted from each electron source 15a. The electron beam emitted from each electron source 15a is focused by electrostatic lens 15d and the focused electron beam collides with each target 15b, which causes radiation to be emitted from each target 15b. The radiation is emitted to first grating 2 after passing through subject 10. The emitted radiation is diffracted by first grating 2 and forms a Talbot interference image at a predetermined distance from first grating 2 in the optical axis direction of the radiation.

This phenomenon is called the Talbot effect, and when an optical wave passes through a grating, a self-image of the grating is formed at a predetermined distance from the grating. For example, when first grating 2 is a phase modulation grating that gives a phase modulation of 90°, a self-image of first grating 2 is formed at a distance given by Formula (2) above (Formula (3) above, if first grating 2 is a phase modulation grating that gives a phase modulation of 180° or an amplitude modulation grating). Here, the wavefront of radiation incident on first grating 2 is distorted by subject 10 so that the self-image of first grating 2 is deformed according to the wavefront distortion.

Then, the radiation passes through second grating 3. As a result, the deformed self-image of first grating 2 is intensity modified through superimposition with second grating 3 and detected by radiation image detector 4 as an image reflecting the wavefront distortion.

Then, second diffraction grating 3 is shifted by shifting mechanism 5 in X direction by 1/n (n is an integer not less than 2) of pitch $P_2$ of the second members, and an image signal reflecting n wavefront distortions is detected by radiation image detector 4.

The image signal reflecting n types of wavefront distortions is inputted to phase image acquisition unit 6, and phase image acquisition unit 6 generates a phase image by analyzing the image reflecting n types of wavefront distortions. The wavefront distortion is proportional to the bent angle of the radiation caused by the diffraction effect of subject 10. Accordingly, amounts depending on the refractive index distribution inside of subject 10 may be detected by analyzing the amount of phase modulation at each pixel from the image reflecting n types of wavefront distortions detected by radiation image detector 4.

Now, in the radiation phase contrast imaging apparatus of the present embodiment, a method of controlling the emission of an electron beam from electron source 15a of each radiation source 1a so that the interval $P_0$ between each focus of radiation of radiation source 1a becomes more appropriate, that is, more appropriate phase image is obtained will be described.

First, radiation is emitted from each radiation source 1a in the same manner as described above without subject 10 being present. Here, it is assumed that electron source 15a that emits an electron beam is already set.

The radiation emitted from each radiation source 1a passes through first grating 2 and second grating 3 in the same manner as described above and is emitted onto radiation image detector 4. Here, it is assumed that first grating 2 and second grating 3 are fixed at predetermined positions.

Then, the focus interval is adjusted such that the contrast of moiré fringe pattern in radiation image detected by radiation image detector 4 becomes maximum.

More specifically, the focus interval is sequentially adjusted by selecting a certain electron source 15a from all of electron sources 15a and emitting an electron beam from only the selected electron source 15a by electron beam emission control unit 16. Then with respect to each focus interval, a moiré fringe pattern produced through superimposition of self-image of the first grating with the second grating is detected by radiation image detector 4.

Figure 7A:
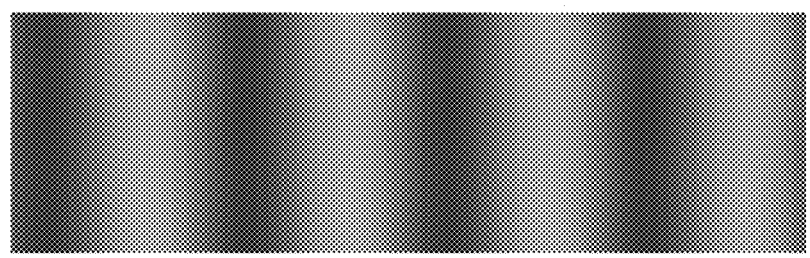
FIGS. 7A to 7C illustrate examples of interference patterns detected by changing the focus interval of the radiation.
Figure 7B:
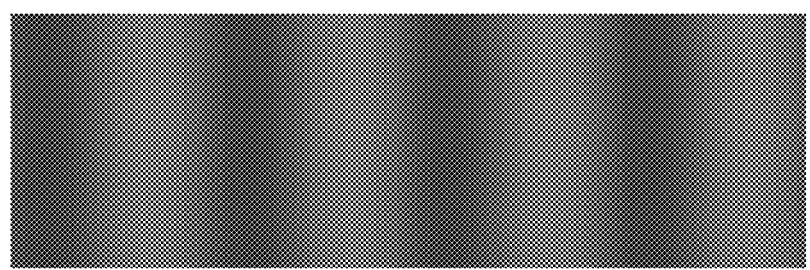
Figure 7C:
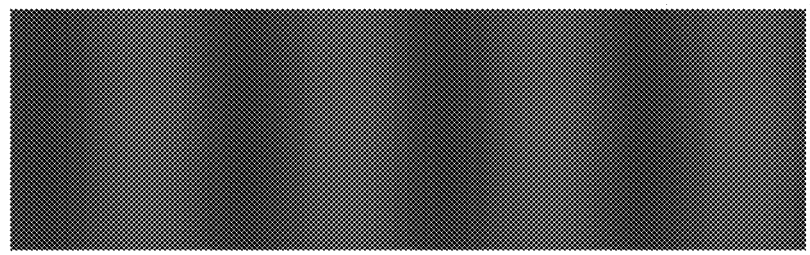
Figure 8:
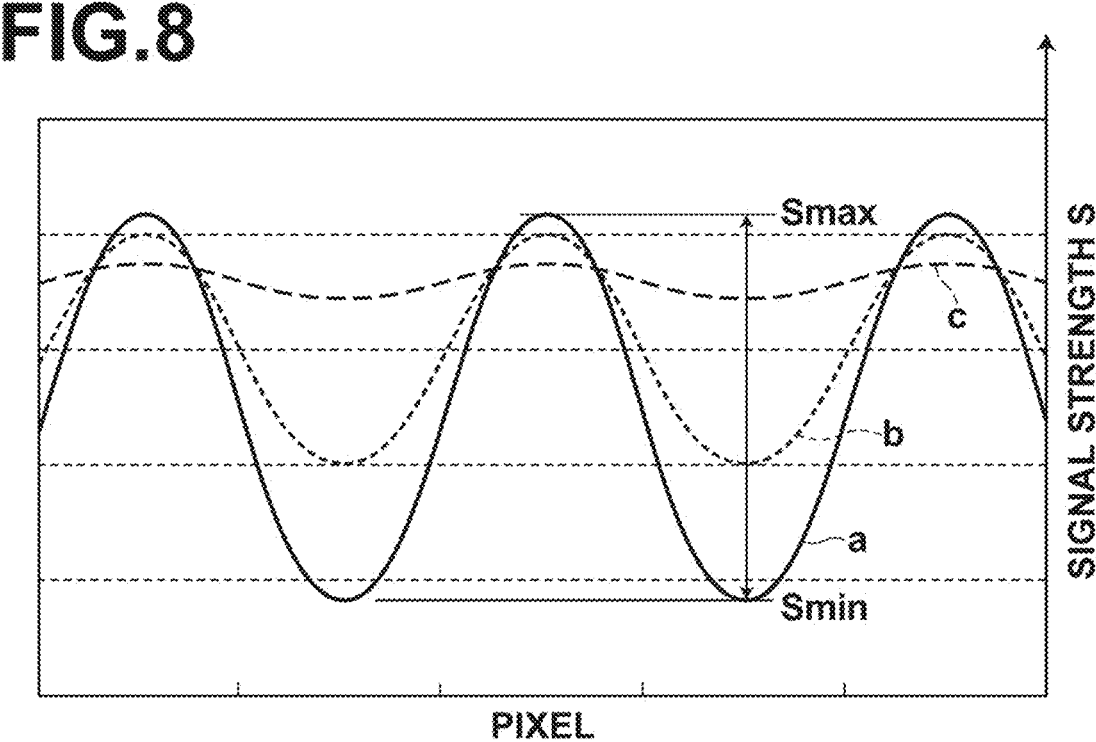
FIG. 8 illustrates intensities of signals representing interference patterns shown in FIG. 7.

FIGS. 7A to 7C illustrate an example of three types of moiré fringe patterns detected by radiation image detector 4 when focus interval of radiation is sequentially changed. Further, FIG. 8 shows intensities of radiation image signals representing the moiré fringe patterns shown in FIG. 7A to 7C. In FIG. 8, the curve "a" is the radiation image signal representing the moiré fringe pattern of FIG. 7A, the curve "b" is the radiation image signal representing the moiré fringe pattern of FIG. 7B, and the curve "c" is the radiation image signal representing the moiré fringe pattern of FIG. 7C.

The image signal representing the moiré fringe pattern with respect to each focus interval like that shown in FIG. 8 is inputted to electron beam emission control unit 16. Then, electron beam emission control unit 16 obtains a maximum value Smax and a minimum value Smin like those shown in FIG. 8 for the image signal representing each moiré fringe pattern. Then, electron beam emission control unit 16 calculates the formula below based on the maximum value Smax and minimum value Smin to obtain an index Cm of contrast of the moiré fringe pattern.

Cm=(Smax−Smin)/(Smax+Smin)

Then, electron beam emission control unit 16 stores the position of electron source 15a corresponding to the focus interval when the Cm becomes maximum.

Thereafter, when a phase image of subject 10 is obtained, electron beam emission control unit 16 performs control such that an electron beam is emitted only from the electron source 15a whose position has been stored in the manner describe above.

In the description above, the Cm calculated by the formula above is used as the contrast index of a moiré fringe pattern, but the contrast index is not limited to this, and the ratio between the maximum value Smax and minimum value Smin or simply the maximum value Smax may be used as the contrast index of a moiré fringe pattern, and the position of electron source 15a corresponding to the focus interval of radiation when such value becomes maximum. Alternatively, simply the minimum value smin may be used as the contrast index, and the position of electron source 15a corresponding to the focus interval of radiation when such value becomes minimal.

Further, in the radiation phase contrast imaging apparatus according to the first embodiment, an electron beam emitted from electron source 15a is controlled by electron beam emission control unit 16 by selectively switching the high voltage applied between extraction electrode 15c and target 15b, thereby controlling the focus interval of the radiation but, for example, the interval between each electron beam emitted from each electron source 15a may be controlled by controlling the electric field formed by electrostatic lens 15d and whereby focus interval of radiation may be controlled.

Figure 9:
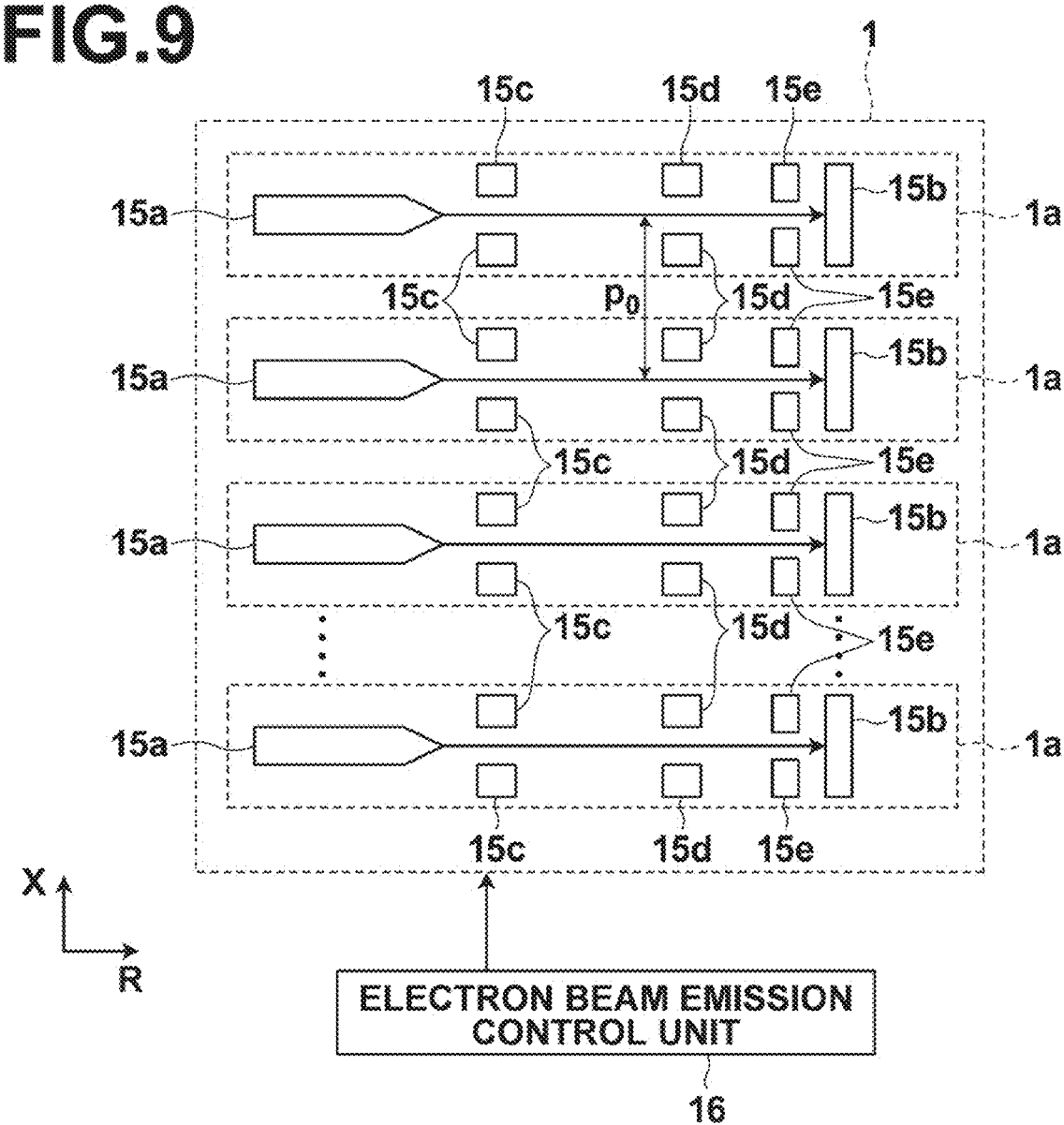
FIG. 9 illustrates a modification of the radiation source.

Still further, in radiation sources 1a of the first embodiment, emission of electron beam emitted from each electron source 15a onto each target 15b may be controlled by further providing gate electrode 15e between each electron source 15a and each target 15b as shown in FIG. 9, then applying a negative voltage to gate electrode 15e, and controlling the magnitude of the negative voltage. More specifically, the emission of radiation from each target 15b is controlled by transmitting/shielding each electron beam emitted from each electron source 15a by controlling the negative voltage applied to each gate electrode 15e. Then, the electron beam emitted onto each target 15b may be controlled by electron beam emission control unit 16 by selectively switching the negative voltage applied to each gate electrode 15e, whereby the focus interval of radiation may be controlled.

Each electron source 15a of each radiation source 1a according to the present embodiment may be formed by patterning an electrode material, such as a carbon nanotube, on a substrate by device processing, such as photolithography. Electron sources of spint type, carbon nanotube type, and surface conduction type may be used.

In the discussion above, the description has been made of a case in which subject 10 is placed between radiation emission unit 1 and first grating 2. In a case where subject 10 is placed between first grating 2 and second grating 3, the self-image of first grating 2 produced at the position of second grating 3 is also deformed by subject 10. Therefore, in this case, an image signal of a phase component modulated by subject 10 can be detected by radiation image detector 4. That is, in the radiation phase contrast imaging apparatus according to the present embodiment, subject 10 may be placed between radiation emission unit 1 and first grating 2 or between first grating 2 and second grating 3.

Figure 10:
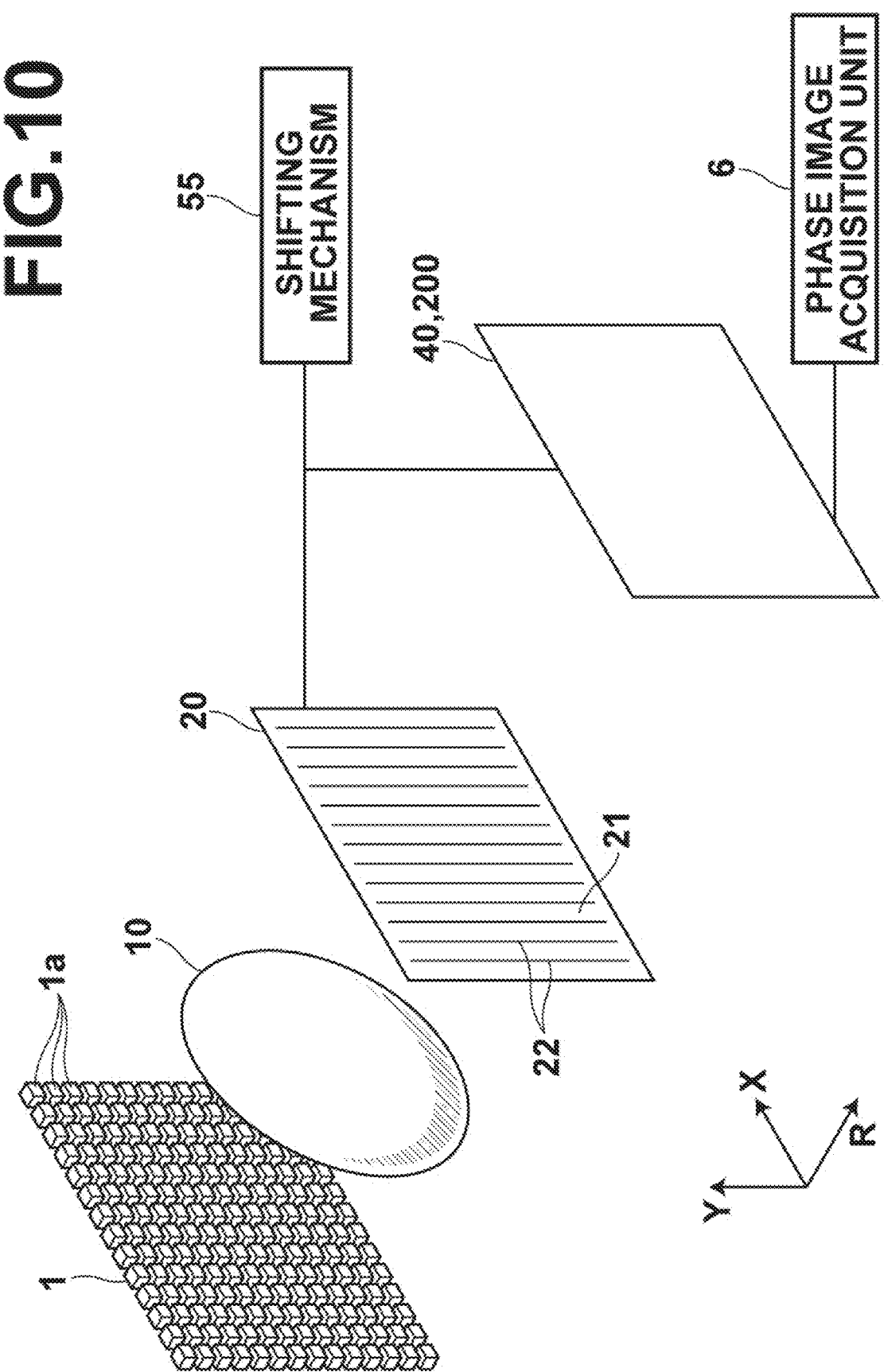
FIG. 10 is a schematic construction diagram of a second or a third embodiment of the radiation phase contrast imaging apparatus of the present invention.
Figure 11:
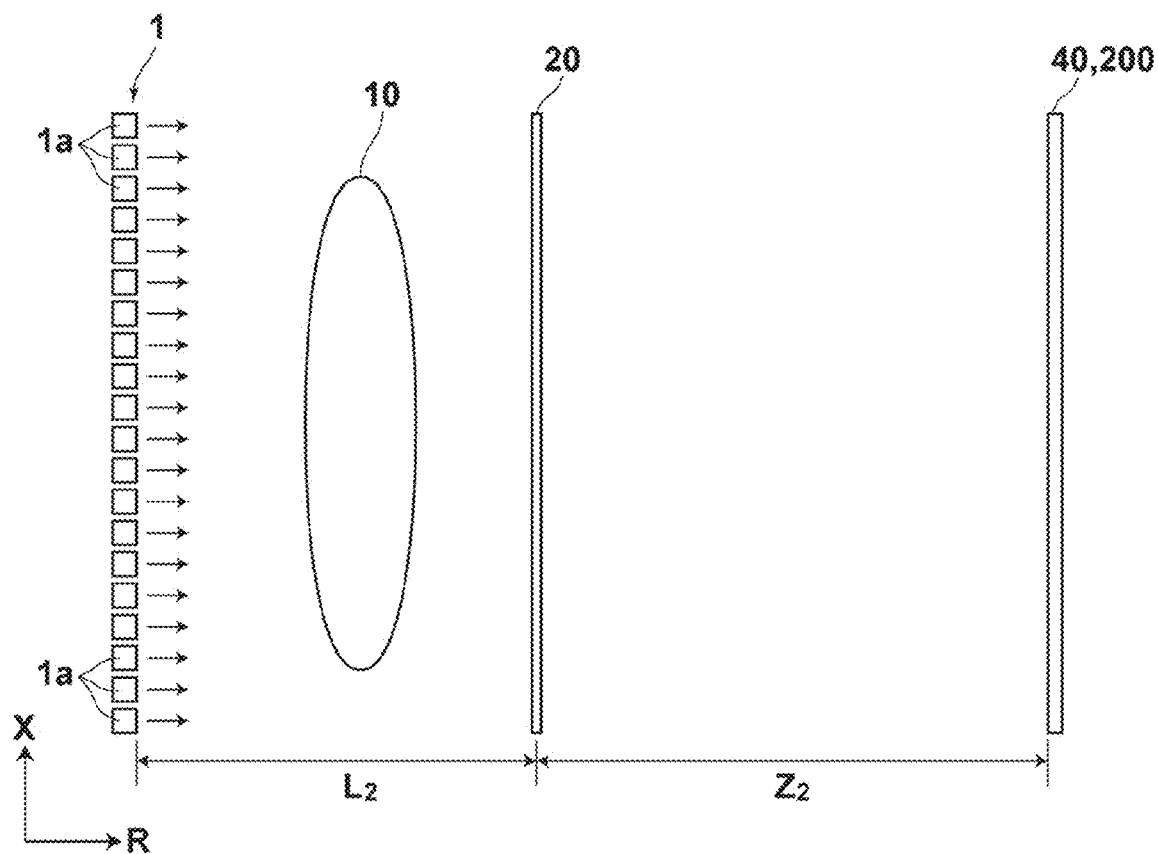
FIG. 11 is a top view of the radiation phase contrast imaging apparatus shown in FIG. 10.

A second embodiment of the radiation phase contrast imaging apparatus of the present invention will be described. FIG. 10 schematically illustrates a construction of the radiation phase contrast imaging apparatus according to the second embodiment. FIG. 11 is a top view (X-R cross-section) of the radiation phase contrast imaging apparatus shown in FIG. 10. The thickness direction in FIG. 11 corresponds to Y direction in FIG. 11.

The radiation phase contrast imaging apparatus according to the second embodiment uses periodic information imaging radiation image detector 40 instead of radiation image detector 4 of radiation phase contrast imaging apparatus according to the first embodiment and does not employ second grating 3.

As illustrated in FIG. 10, the radiation phase contrast imaging apparatus according to the second embodiment includes radiation emission unit 1 that emits radiation onto subject 10, grating 20 for receiving the radiation transmitted through subject 10 and diffracting the radiation, periodic information imaging radiation image detector 40 for detecting periodic information of the radiation diffracted by grating 20, shifting mechanism 55 for shifting grating 20 and periodic information imaging radiation image detector 40 in a direction orthogonal to linear electrodes of detector 40 (X direction in FIG. 10) along the respective planes, and phase image acquisition unit 6 for forming a phase image based on an image signal detected by periodic information imaging radiation image detector 40.

Radiation emission unit 1 has an identical structure to that of the first embodiment.

Grating 20 has an identical structure to that of the first grating in the radiation phase contrast imaging apparatus according to the first embodiment.

In the second embodiment, a radiation phase contrast imaging apparatus capable of obtaining a radiation phase image is configured by grating 20 and periodic information imaging radiation image detector 40. But, in order to make this configuration function as a Talbot interferometer, the configuration must further substantially satisfy several conditions, which will be described hereinafter.

The distance $Z_2$ between grating 20 and periodic information imaging radiation image detector 40 must substantially satisfy the condition below when grating 20 is a phase modulation grating that gives a phase modulation of 90°.

$$Z_2 = \left(m + \frac{1}{2}\right)\frac{P_1^2}{\lambda} \tag{4}$$

where, $\lambda$ is the wavelength of radiation (normally, center wavelength), m is 0 or a positive integer, and $P_1$ is the grating pitch of grating 20.

Further, the distance $Z_2$ between grating 20 and periodic information imaging radiation image detector 40 must substantially satisfy the condition below when grating 20 is a phase modulation grating that gives a phase modulation of 180° or an amplitude modulation grating.

$$Z_2 = (m+1)\frac{P_1^2}{\lambda} \tag{5}$$

Figure 12:
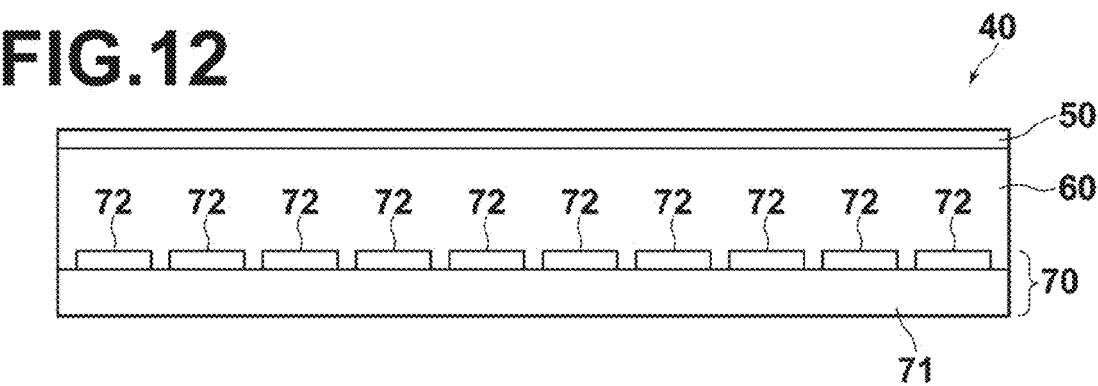
FIG. 12 is a cross-sectional view of a periodic information imaging radiation image detector of the radiation phase contrast imaging apparatus according to the second embodiment, illustrating a schematic construction thereof.

The structure of periodic information imaging radiation image detector 40 in the radiation phase contrast imaging apparatus of the present embodiment will now be described in detail. FIG. 12 is a partial sectional view of periodic information imaging radiation image detector 40.

As illustrated in FIG. 12, periodic information imaging radiation image detector 40 includes active matrix substrate 70, semiconductor layer 60 formed on substantially the entire surface of the active matrix substrate 70, and upper electrode 50.

Semiconductor layer 60 has electromagnetic wave conductivity and generates charges therein when exposed to radiation. As for semiconductor layer 60, for example, a selenium based amorphous Se film with a thickness of 10 to 1500 μm may be used. Alternatively, $PbI_2$, $HgI_2$, $Cd(Zn)Te$, $Bi_{12}TiO_{20}$, $Bi_{12}SiO_{20}$, or $Bi_{12}GeO_{20}$ may also be used. Semiconductor layer 60 is formed on active matrix substrate 70 by a vacuum deposition method or the like.

Upper electrode 50 is formed of a conductive material having a low resistance, such as Au, Al, or the like, with a thickness capable of transmitting emitted radiation. Note that intermediate layers may be provided between upper electrode 50 and semiconductor layer 60. Such intermediate layers include a charge transport layer for preventing charge injection from upper electrode 50 and allowing charges of those generated in the semiconductor layer having opposite polarity to that of injected charges to reach upper electrode 50, a crystallization prevention layer for preventing crystallization of the amorphous Se, and the like.

As illustrated in FIG. 12, active matrix substrate 70 includes glass substrate 71 on which multiple unit elements 72, which include charge collection electrodes and switch elements corresponding to pixels forming radiation image of a subject, are disposed two-dimensionally.

Figure 13:
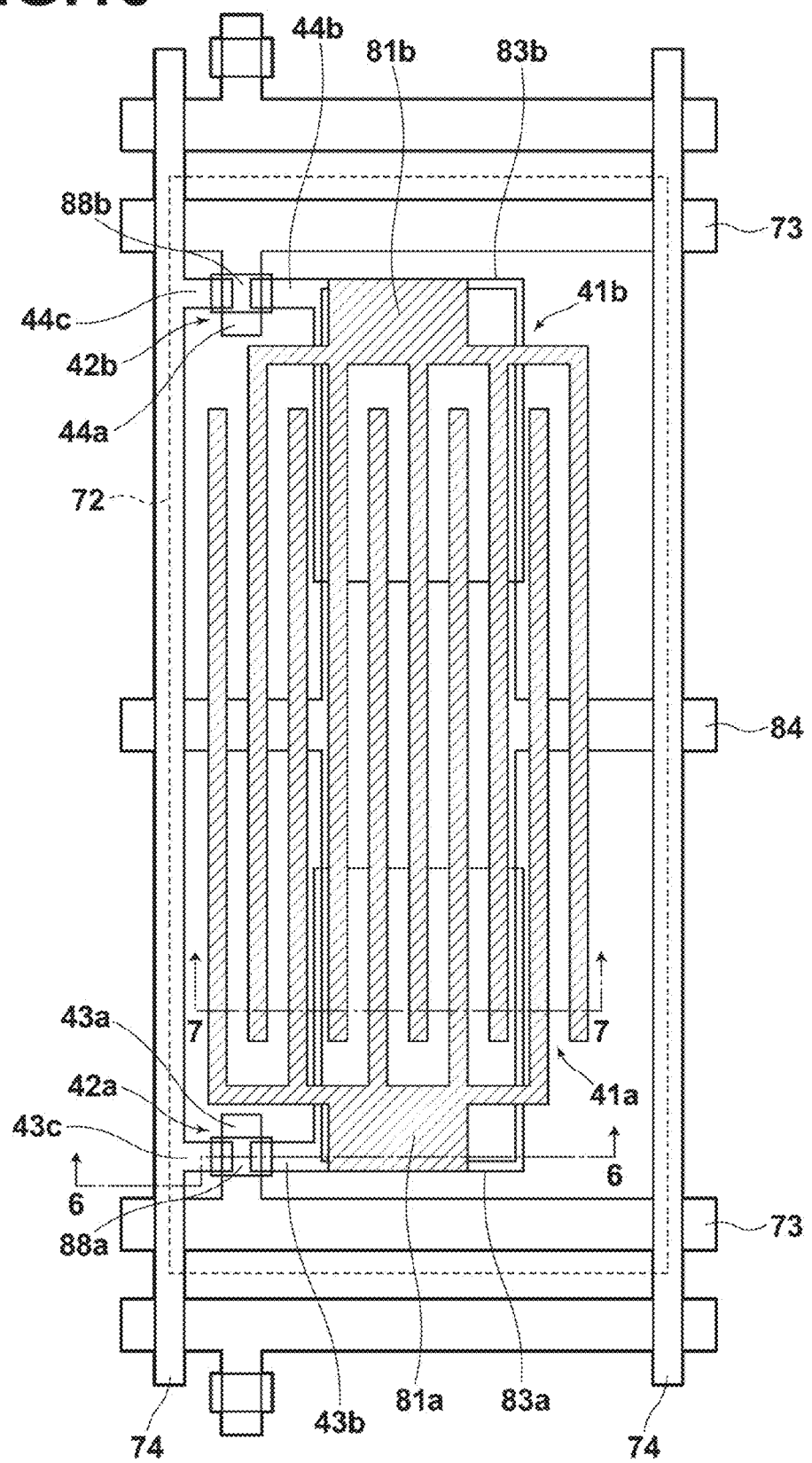
FIG. 13 is a partial plan view of the periodic information imaging radiation image detector.
Figure 14:
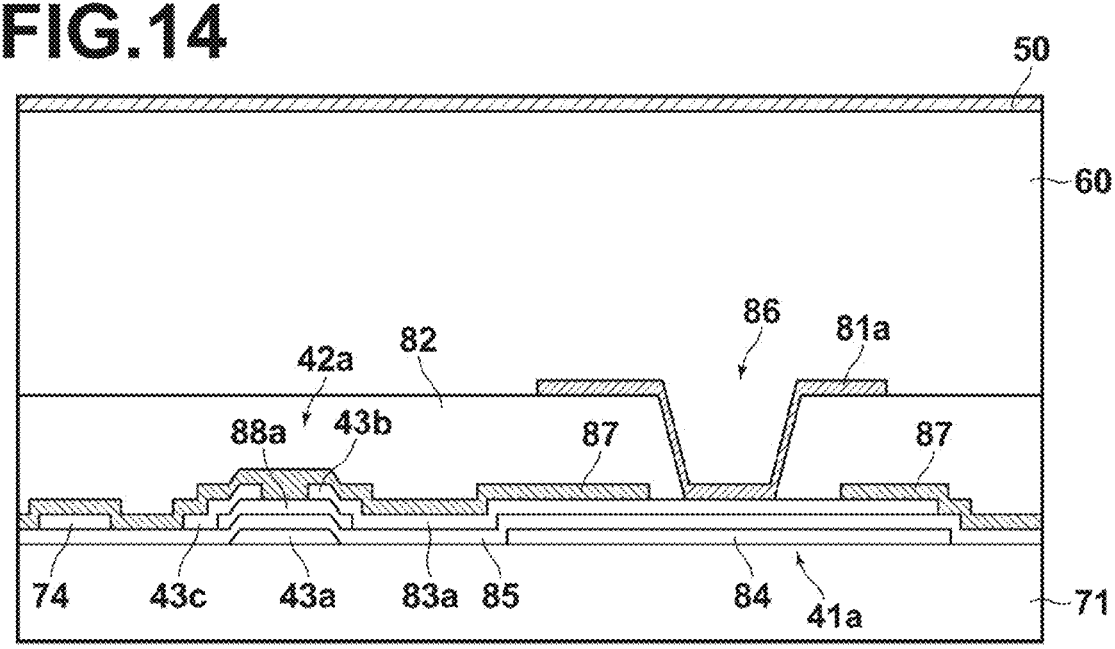
FIG. 14 is a cross-sectional view of the partial periodic information imaging radiation image detector taken along the line 6-6 in FIG. 13.
Figure 15:
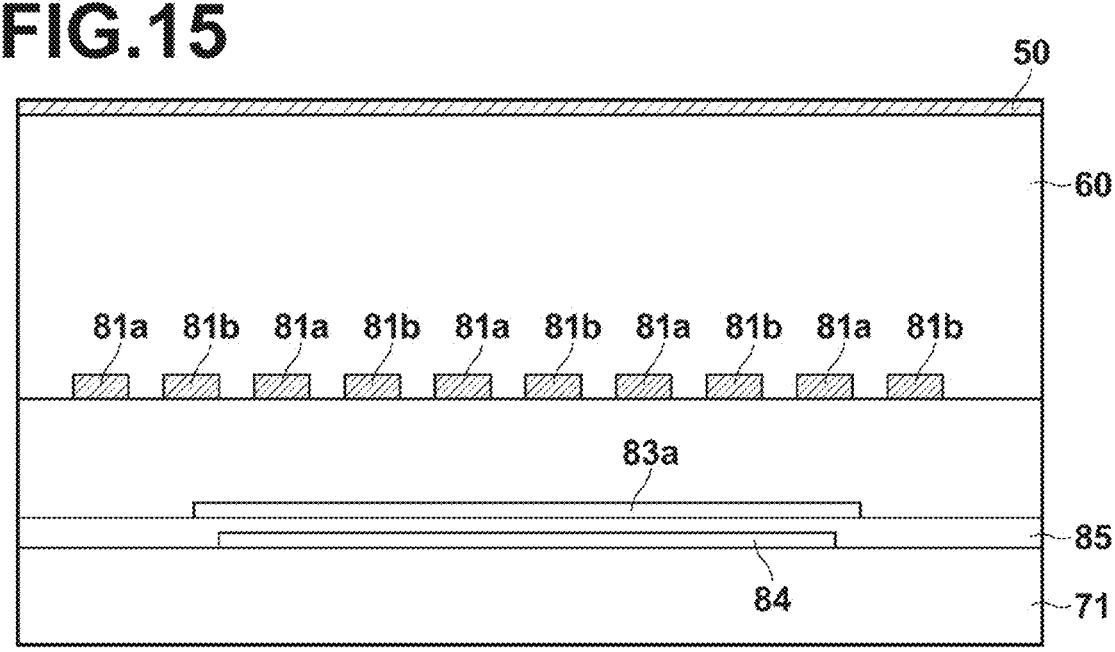
FIG. 15 is a cross-sectional view of the partial periodic information imaging radiation image detector taken along the line 7-7 in FIG. 13.

The structure of each pixel or sub-pixel of periodic information imaging radiation image detector 40 will now be described in detail. The term "sub-pixel" as used herein refers to a pair of two linear electrode groups alternately disposed such that the phase of the arrangement period become opposite to each other. FIG. 13 is a plan view of periodic information imaging radiation image detector 40, FIG. 14 is a cross-sectional view of periodic information imaging radiation image detector 40 taken along the line 6-6 in FIG. 13, and FIG. 15 is a cross-sectional view of periodic information imaging radiation image detector 40 taken along the line 7-7 in FIG. 13.

Periodic information imaging radiation image detector 40 includes a charge collection electrode, constituted by first linear electrode group 81a and second linear electrode group 81b, for collecting charges generated in semiconductor layer 60, first storage capacitor 41a for storing charges collected by first linear electrode group 81a, second storage capacitor 41b for storing charges collected by second linear electrode group 81b, a first TFT switch 42a for reading out the charges stored in first storage capacitor 41a, a second TFT switch 42b for reading out the charges stored in second storage capacitor 41b.

Figure 16:
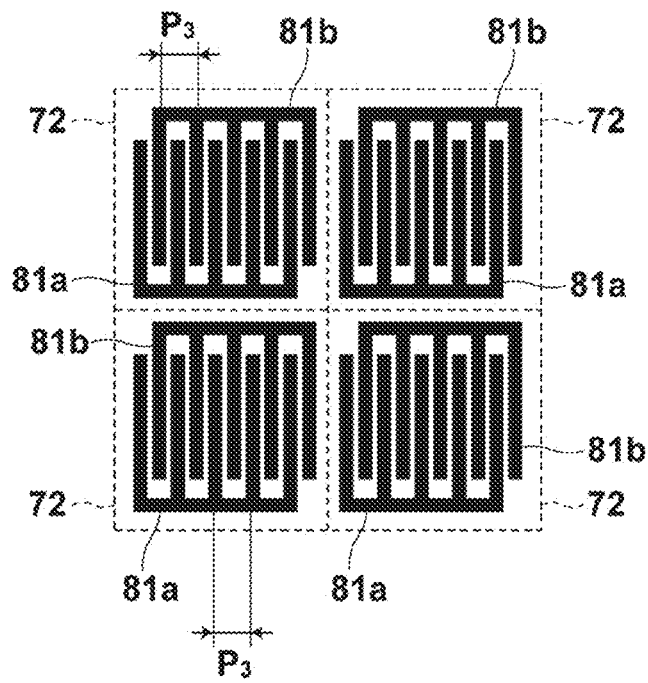
FIG. 16 is a schematic view of first linear electrode groups and second linear electrode groups of unit elements corresponding to four pixels.

FIG. 16 schematically illustrates first linear electrode groups 81a and second linear electrode groups 81b of unit elements 72 corresponding to four pixels. Each of first linear electrode group 81a and second linear electrode group 81b includes multiple linear electrodes periodically disposed with a pitch of $P_3$. A linear electrode of second linear electrode group 81b is disposed between linear electrodes of first linear electrode group 81a such that the phase of the arrangement period of linear electrodes of first linear electrode groups 81a and the phase of the arrangement period of linear electrodes of second linear electrode group 81b are shifted by π (180°=a half of the pitch) from each other. As illustrated in FIG. 16, linear electrodes of first linear electrode group 81a are connected to each other, and linear electrodes of second linear electrode group 81b are connected to each other. Preferably, the connection wire connecting the linear electrodes is provided on a different plane from that of the linear electrodes so as not to function as an electrode, but the influence of the connection wire may be substantially reduced to a negligible level by reducing the width of the connection wire.

Arrangement pitch $P_3$ of linear electrodes of first linear electrode group 81a and arrangement pitch $P_3$ of linear electrodes of second linear electrode group 81b are set to a value in the range from 2 to 15 μm. The width of each linear electrode of first linear electrode group 81a and the width of each linear electrode of second linear electrode group 81b are set to a value in the range from 1 to 14 μm.

Here, in the present embodiment, the focus of radiation corresponding to each electron source 15a, grating 20, and periodic information imaging radiation image detector 40 are disposed at predetermined distances in the optical axis direction of the radiation.

More specifically, the radiation phase contrast imaging apparatus of the present embodiment is configured such that the interval $P_0$ between the center of each focus of radiation corresponding to each electron source 15a, the distance $L_2$ (FIG. 11) between the focus and grating 20, the distance $Z_2$ (FIG. 11) between grating 20 and periodic information imaging radiation image detector 40, and interval $P_3$ (FIG. 16) between linear electrodes constituting periodic information imaging radiation image detector 40 satisfy Formula (6) below.

$$P_0 = P_3 \times L_2 / Z_2 \qquad (6)$$

With respect to the interval $P_0$ between each focus of radiation corresponding to each electron source 15a, it is possible to dispose each electron source 15a in advance at an interval that satisfies Formula (6) above, or the interval may be adjusted to $P_0$ by outputting electron beams from only a certain electron source 15a through control of electron beam emission control unit 16.

Even when each electron source 15a is disposed, in advance, at an appropriate interval $P_0$ that satisfies Formula (6) above, it often may be displaced from the desired position because of various causes of system perturbation, e.g., a device manufacturing error from design interval $P_0$, a geometrical displacement over time. In such a case, the interval may be adjusted to $P_0$ by emitting electron beams from only a certain electron source 15a through control of electron beam emission control unit 16. The method for selecting a certain electron source 15a, when emitting electron beams from only a certain electron source 15a, is identical to that of the radiation phase contrast imaging apparatus of the first embodiment.

First linear electrode group 81a and second linear electrode group 81b may be formed of, for example, an amorphous transparent conductive oxide film.

Note that intermediate layers may be provided between first and second linear electrode groups 81a, 81b and semiconductor layer 60. Such intermediate layers include a charge transport layer for preventing charge injection from the electrodes and collecting charges generated in semiconductor layer 60 by first linear electrode group 81a and second linear electrode group 81b, a crystallization prevention layer for preventing crystallization of the amorphous Se, and the like.

First storage capacitor 41a is constituted by connection electrode 83a, gate insulation film 85, and charge storage capacitor electrode 84, in which gate insulation film 85 acts as a dielectric body and charges are stored between connection electrode 83a and charge storage capacitor electrode 84. Second storage capacitor 41b is constituted by connection electrode 83b, gate insulation film 85, and charge storage capacitor electrode 84, in which gate insulation film 85 acts as a dielectric body and charges are stored between connection electrode 83b and charge storage capacitor electrode 84.

First TFT switch 42a is constituted by gate electrode 43a formed by extending scanning wire 73, to be described later, drain electrode 43b formed by extending connection electrode 83a, source electrode 43c formed by extending data wire 74, to be described later, gate insulation film 85, semiconductor film 88a, and the like. Second TFT switch 42b is constituted by gate electrode 44a formed by extending scanning wire 73, drain electrode 44b formed by extending connection electrode 83b, source electrode 44c formed by extending data wire 74, gate insulation film 85, semiconductor film 88b, and the like. For example, gate insulation film 85 is formed of $SiN_x$, $SiO_x$, or the like. Semiconductor films 88a, 88b are channel sections of first and second TFT switches 42a, 42b, which are current paths connecting data wire 74 to connection electrodes 83a, 83b.

Insulation protection film 87 is formed so as to cover first storage capacitor 41a and second storage capacitor 41b, first TFT switch 42a and second TFT switch 42b, data wire 74, and the like. Contact holes 86 are formed in insulation protection film 87 at a connection section between first linear electrode group 81a and connection electrode 83a, and at a connection section between second linear electrode group 81b and connection electrode 83b.

Interlayer insulation film 82 is formed on insulation protection film 87 and contact holes 86 are formed through the interlayer insulation film 82, through which first linear electrode group 81a is connected to connection electrode 83a, and second linear electrode group 81b is connected to connection electrode 83b. Interlayer insulation film 82 is an organic insulation film for electrically insulating and isolating first TFT switch 42a from second TFT switch 42b. For example, an acrylic resin may be used as the material of the organic insulation film.

As illustrated in FIG. 15, scanning wires 73 and data wires 74 are electrode wires disposed in a grid pattern, and first TFT switch 42a or second TFT switch 42b is formed adjacent to each intersection point. Different scanning wires 73 are connected to first TFT switch 42a and second TFT switch 42b, and first TFT switch 42a and second TFT switch 42b are configured to be ON/OFF controlled independently.

A readout circuit (not shown) constituted by an amplifier for detecting a signal charge flowing out to data wire 74 is connected at the end of data wire 74. A gate driver (not shown) that outputs control signals for independently controlling first TFT switch 42a and second TFT switch 42b is connected to scanning wire 73.

As described above, shifting mechanism 55 is a mechanism for shifting grating 20 or periodic information imaging radiation image detector 40 in X direction. For example, grating 20 and periodic information imaging radiation image detector 40 may be shifted by 1/n (n is an integer not less than 2) of arrangement pitch $P_3$ of the linear electrodes of periodic information imaging radiation image detector 40 to take a radiation image at each position, whereby image signals of n-types of phase components may be obtained. As in the first embodiment, from the n types of image signals, the amount of differential phase shift with respect to each pixel, that is, an amount corresponding to a diffraction angle of radiation caused by subject 10 may be restored, which may be provided as a so-called phase contrast image through various types of image processing and representations. It is preferable, for example, to shift periodic information imaging radiation image detector 40 such that image signals corresponding to four or six types of phase components are obtained. When the charge collection electrode is formed of first linear electrode group 81a and second linear electrode group 81b, as in the present embodiment, four types of phase components may be obtained by shifting detector 40 by ½ of arrangement pitch $P_3$ and six types of phase components may be obtained by shifting detector 40 by ⅓ of arrangement pitch $P_3$. When forming a phase image with signals corresponding to two types of phase components, shifting mechanism is not required.

Next, an operation of the radiation phase contrast imaging apparatus according to the present embodiment for recording a radiation image and reading out from the periodic information imaging radiation image detector will be described.

First, subject 10 is placed between radiation emission unit 1 and grating 20 (FIG. 11). In the radiation phase contrast imaging apparatus according to the present embodiment, subject 10 is placed between radiation emission unit 1 and grating 20, but subject 10 may be placed between grating 20 and periodic information imaging radiation image detector 40. In this case, the distance from the subject to periodic information imaging radiation image detector 40 becomes shorter and the magnification rate is reduced, which allows the apparatus to be easily installed in an existing radiography room.

Then, in each radiation source 1a of radiation emission unit 1, a high voltage is applied between extraction electrode 15c and target 15b and a voltage is applied between electron source 15a and extraction electrode 15c, which causes an electron beam to be emitted from each electron source 15a. The electron beam emitted from each electron source 15a is focused by electrostatic lens 15d and the focused electron beam collides with each target 15b, which causes radiation to be emitted from each target 15b. The radiation is emitted to grating 20 after passing through subject 10. The emitted radiation is diffracted by grating 20 and a self-image of grating 20 is formed at a predetermined distance from grating 20 in the optical axis direction of the radiation.

For example, when grating 20 is a phase modulation grating that gives a phase modulation of 90°, a self-image of grating 20 is formed at a distance given by Formula (4) above (Formula (3) above, if grating 20 is a phase modulation grating that gives a phase modulation of 180° or an amplitude modulation grating). Here, the wavefront of radiation incident on grating 20 is distorted by subject 10 so that the self-image of grating 20 is deformed according to the wavefront distortion.

Then, with a positive voltage being applied to upper electrode 50 of periodic information imaging radiation image detector 40 by a voltage source, the radiation representing the self-image formed by the grating 20 in the manner as described above is emitted to periodic information imaging radiation image detector 40 from the side of upper electrode 50. In the radiation phase contrast imaging apparatus of the present embodiment, periodic information imaging radiation image detector 40 is disposed such that upper electrode 50 faces radiation emission unit 1 and the length direction of each linear electrode of first and second linear electrode groups 81a and 81b of active matrix substrate 70 corresponds to the length direction of each member 22 of grating 20.

The radiation emitted on periodic information imaging radiation image detector 40 transmits through upper electrode 50 and reaches semiconductor layer 60. Then, semiconductor layer 60 generates charge pairs by the exposure of the radiation, and negative charges of the charge pairs are combined with positive charges charged on upper electrode 50 and dissolved, while positive charges of the charge pairs are collected by first and second linear electrode groups 81a, 81b of each unit element 72, and stored in first and second storage capacitors 41a, 41b.

Figure 17:
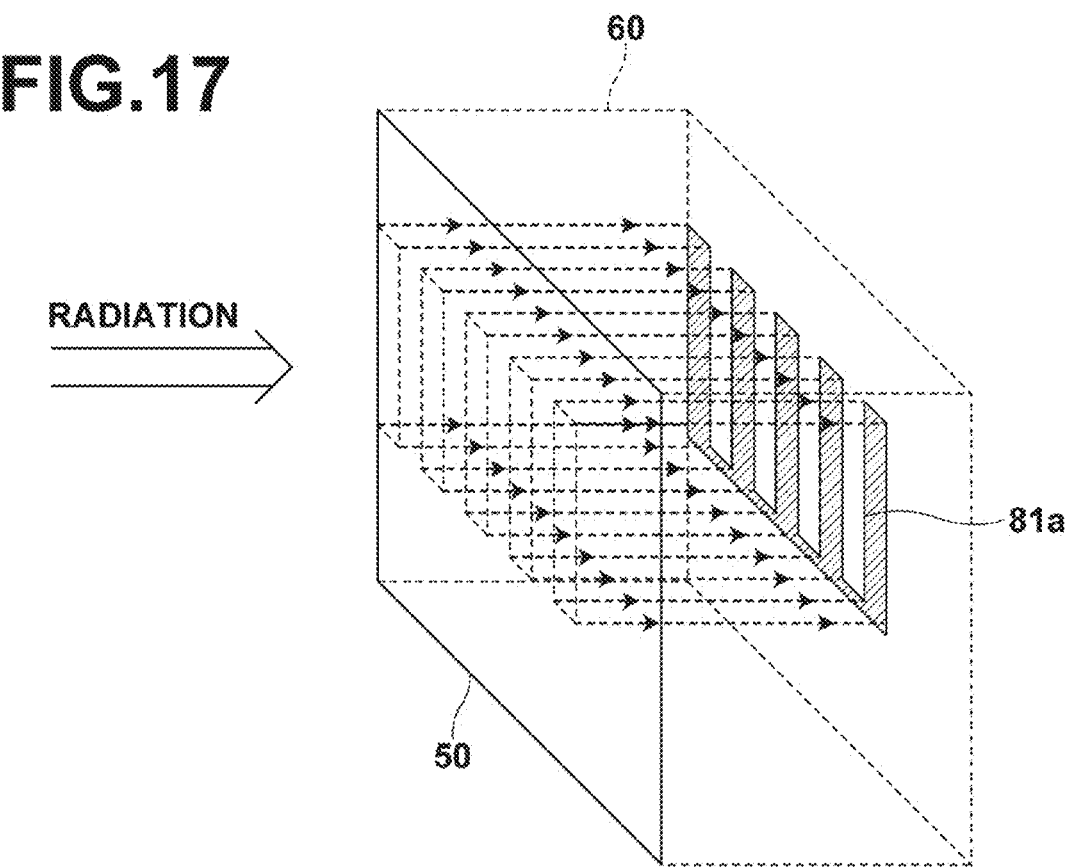
FIG. 17 illustrates an electric field formed in a semiconductor layer by the first linear electrode group.

Here, in periodic information imaging radiation image detector 40 of radiation phase contrast imaging apparatus of the present embodiment, the charge collection electrode for collecting charges generated in semiconductor layer 60 is constituted by first linear electrode group 81a and second linear electrode group 81b. Therefore, when a voltage is applied to upper electrode 50 in the manner as described above, electric fields are formed in semiconductor layer 60 toward first and second linear electrode groups substantially parallel to each other, i.e., substantially perpendicular to the surface of upper electrode 50, as illustrated by dotted arrows in FIG. 17. The charges generated in semiconductor layer 60 are collected by first and second linear electrode groups 81a, 81b along the electric fields, so that first and second linear electrode groups 81a, 81b perform a function equivalent to that of the combination of an amplitude diffraction grating and a detector provided in the later stage of the grating. Accordingly, charges representing an intensity modified signal through superimposition of the deformed self-image of grating 20 with a virtual grating formed by first linear electrode group 81a and reflecting the wavefront distortion are stored in first charge capacitor 41a, and charges representing an intensity modified signal through superimposition of the deformed self-image of grating 20 with a virtual grating formed by second linear electrode group 81b and reflecting the wavefront distortion are stored in second charge capacitor 41b. As described above, first linear electrode group 81a and second linear electrode group 81b are phase shifted by $\pi$ from each other, so that signals corresponding to two types of phase components phase shifted from each other by $\pi$ are detected by periodic information imaging radiation image detector 40.

Then, control signals for turning ON first TFT switches 42a are sequentially outputted from the not shown gate driver to each scanning wire 73 connected to first TFT switches 42a. Then, first TFT switches 42a are turned ON according to the control signals outputted from the gate driver, and charges stored in first storage capacitor 41a of each unit element 72 are read out to data wire 74. The charge signal flowed out to data wire 74 is detected by the charge amplifier of a not shown readout circuit as an image signal corresponding to a first phase component.

Then, control signals for turning ON second TFT switches 42b are sequentially outputted from the not shown gate driver to each scanning wire 73 connected to second TFT switches 42b. Then, second TFT switches 42b are turned ON according to the control signals outputted from the gate driver, and charges stored in second storage capacitor 41b of each unit element 72 are read out to data wire 74. The charge signal flowed out to data wire 74 is detected by the charge amplifier of a not shown readout circuit as an image signal corresponding to a second phase component.

Thereafter, periodic information imaging radiation image detector 40 is shifted by shifting mechanism 55, and the image recording in detector 40 and image signal reading from detector 40 are performed at each predetermined position, whereby image signals corresponding to the first and second phase components are detected at each predetermined position.

Image signals detected in the manner as described above are inputted to phase image acquisition unit 6. Then, phase image acquisition unit 6 generates a phase image based on image signals of a plurality of phase components.

Next, a modification of periodic information imaging radiation image detector 40 of radiation phase contrast imaging apparatus according to the second embodiment will be described.

Figure 18:
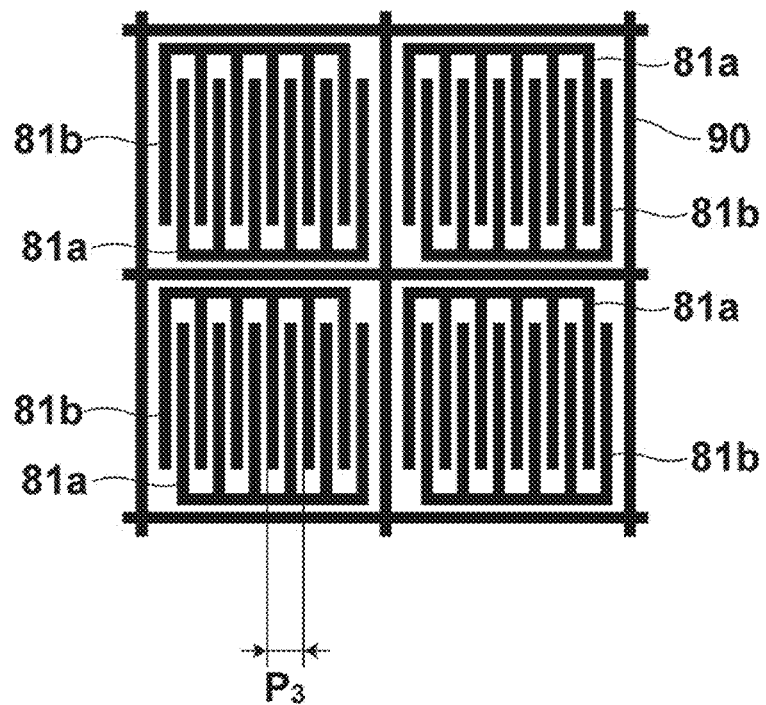
FIG. 18 illustrates a modification of the periodic information imaging radiation image detector of the radiation phase contrast imaging apparatus according to the second embodiment.

In addition to first linear electrode group 81a and second linear electrode group 81b of periodic information imaging radiation image detector 40 shown in FIG. 16, constant potential linear electrode 90 may be provided in a grid pattern enclosing the charge collection electrode, constituted by first and second linear electrode groups 81a, 81b, of each unit element 72, as illustrated in FIG. 18. If a gap is present between charge collection electrodes, electric fields are bent and a charge is collected from a portion where the linear electrode is not present, whereby phase component contamination occurs. Consequently, the provision of constant potential linear electrode 90 to which a constant potential is applied allows stabilization of the electric fields and prevention of the contamination described above. A potential that does not cause a large potential difference with an adjacent charge collection electrode is applied to constant potential linear electrode 90. That is, substantially the same potential as that of the charge collection electrode is applied. More specifically, constant potential linear electrode 90 is set to a ground potential or a value close to the ground potential. Where constant potential linear electrode 90 is provided, it is preferable to arrange and dispose first linear electrode group 81a and second linear electrode group 81b in the manner shown in FIG. 18.

In periodic information imaging radiation image detector 40 of the present embodiment, first linear electrode group 81a and second linear electrode group 81b, phase shifted by $\pi$ from each other, are provided in each unit element 72 as the charge collection electrode. The shape of the charge collection electrode is not limited to this.

Figure 19:
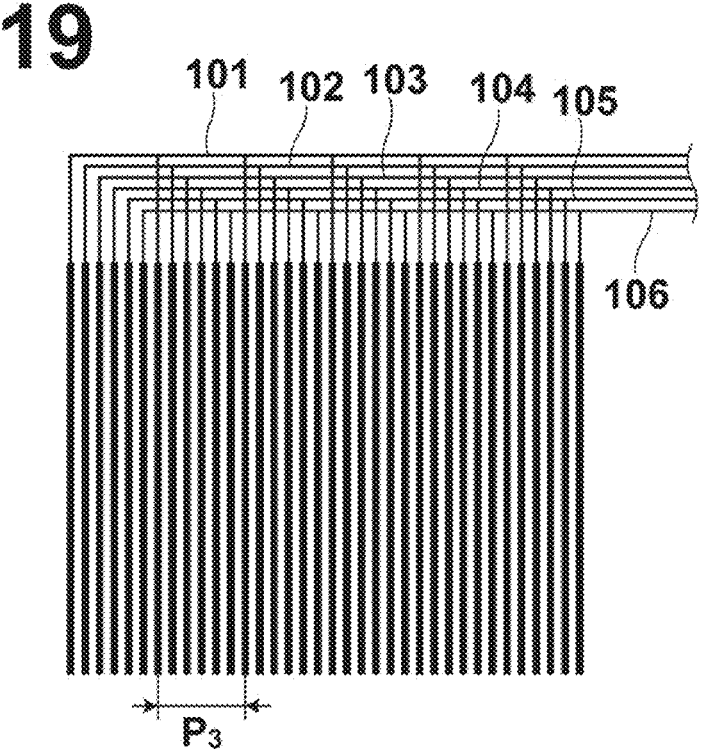
FIG. 19 illustrates a modification of the periodic information imaging radiation image detector of the radiation phase contrast imaging apparatus according to the second embodiment.

For example, first to sixth linear electrode groups 101 to 106, each having multiple linear electrodes arranged with pitch $P_3$, may be disposed such that the phase of the arrangement period of linear electrodes of each linear electrode group is shifted by $\pi/3$ from each other, as illustrated in FIG. 19. More specifically, first to sixth linear electrode groups 101 to 106 may be disposed such that, when the phase of first linear electrode group 101 is assumed to be 0, the phase of second linear electrode group 102 is $\pi/3$, the phase of third linear electrode group 103 is $2\pi/3$, the phase of fourth linear electrode group 104 is $\pi$, the phase of fifth linear electrode group 105 is $4\pi/3$, and the phase of sixth linear electrode group 106 is $5\pi/3$.

Formation of the charge collection electrode in the manner illustrated in FIG. 19 to read out charges collected by first to sixth linear electrode groups 101 to 106 with respect to each linear electrode group allows acquisition of image signals corresponding to six types of phase components having different phases by one image acquiring operation. Accordingly, shifting mechanism 55 is not required.

Figure 20:
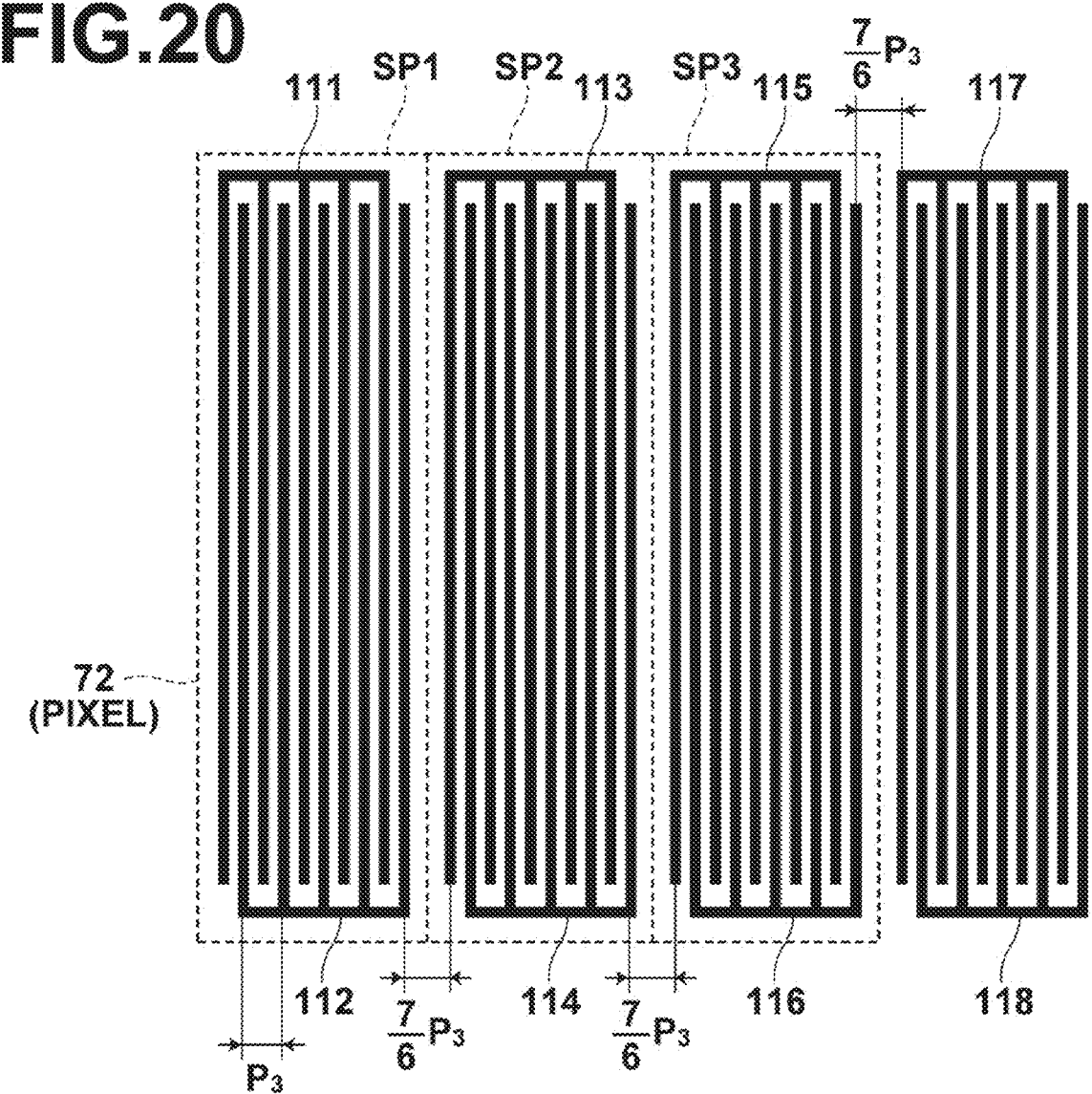
FIG. 20 illustrates a modification of the periodic information imaging radiation image detector of the radiation phase contrast imaging apparatus according to the second embodiment.

Further, as illustrated in FIG. 20, a pixel corresponding to one unit element 72 may be divided into a plurality of sub-pixels (here, three sub-pixels) and linear electrode groups having different phases may be disposed in each sub-pixel. In the present embodiment, the sub-pixel refers to a pair of two linear electrode groups alternately disposed such that the phase of the arrangement period becomes opposite to each other.

More specifically, in the modification shown in FIG. 20, first linear electrode group 111 in which linear electrodes are arranged with pitch $P_3$ and second linear electrode group 112 in which linear electrodes are arranged with pitch $P_3$ are disposed in sub-pixel SP1 so as to have a phase difference of π from each other, third linear electrode group 113 in which linear electrodes are arranged with pitch $P_3$ and fourth linear electrode group 114 in which linear electrodes are arranged with pitch $P_3$ are disposed in sub-pixel SP2 so as to have a phase difference of π from each other, and fifth linear electrode group 115 in which linear electrodes are arranged with pitch $P_3$ and sixth linear electrode group 116 in which linear electrodes are arranged with pitch $P_3$ are disposed in sub-pixel SP3 so as to have a phase difference of π from each other. Then, adjacent linear electrode groups of sub-pixel SP1 and sub-pixel SP2 are disposed at a distance of $(7/6) \times P_3$, and adjacent linear electrode groups of sub-pixel SP2 and sub-pixel SP3 are disposed at a distance of $(7/6) \times P_3$, whereby the phase is shifted by $4\pi/3$ between sub-pixels. Arrangement of the linear electrode groups in one pixel in the manner shown in FIG. 20 results in that, when the phase of first linear electrode group 111 is assumed to be 0, the phase of second linear electrode group 112 is π, the phase of third linear electrode group 113 is $4\pi/3$, the phase of fourth linear electrode group 114 is $\pi/3$, the phase of fifth linear electrode group 115 is $2\pi/3$, and the phase of sixth linear electrode group 116 is $5\pi/3$. Note that linear electrode group 117 and linear electrode group 118 are the linear electrode groups of adjacent pixel.

Formation of the charge collection electrode in the manner illustrated in FIG. 20 to read out charges collected by first to sixth linear electrode groups 111 to 116 with respect to each linear electrode group allows acquisition of image signals corresponding to six types of phase components by one image acquiring operation. The structure of charge collection electrode shown in FIG. 19 also allows acquisition of image signals corresponding to six types of phase components by one image acquiring operation, but the structure of charge collection electrode shown in FIG. 20 allows the use of wider linear electrodes in comparison with the structure of FIG. 19. The spatial resolution is somewhat degraded in the structure shown in FIG. 20, but the structure allows easy connection of linear electrodes.

Figure 21:
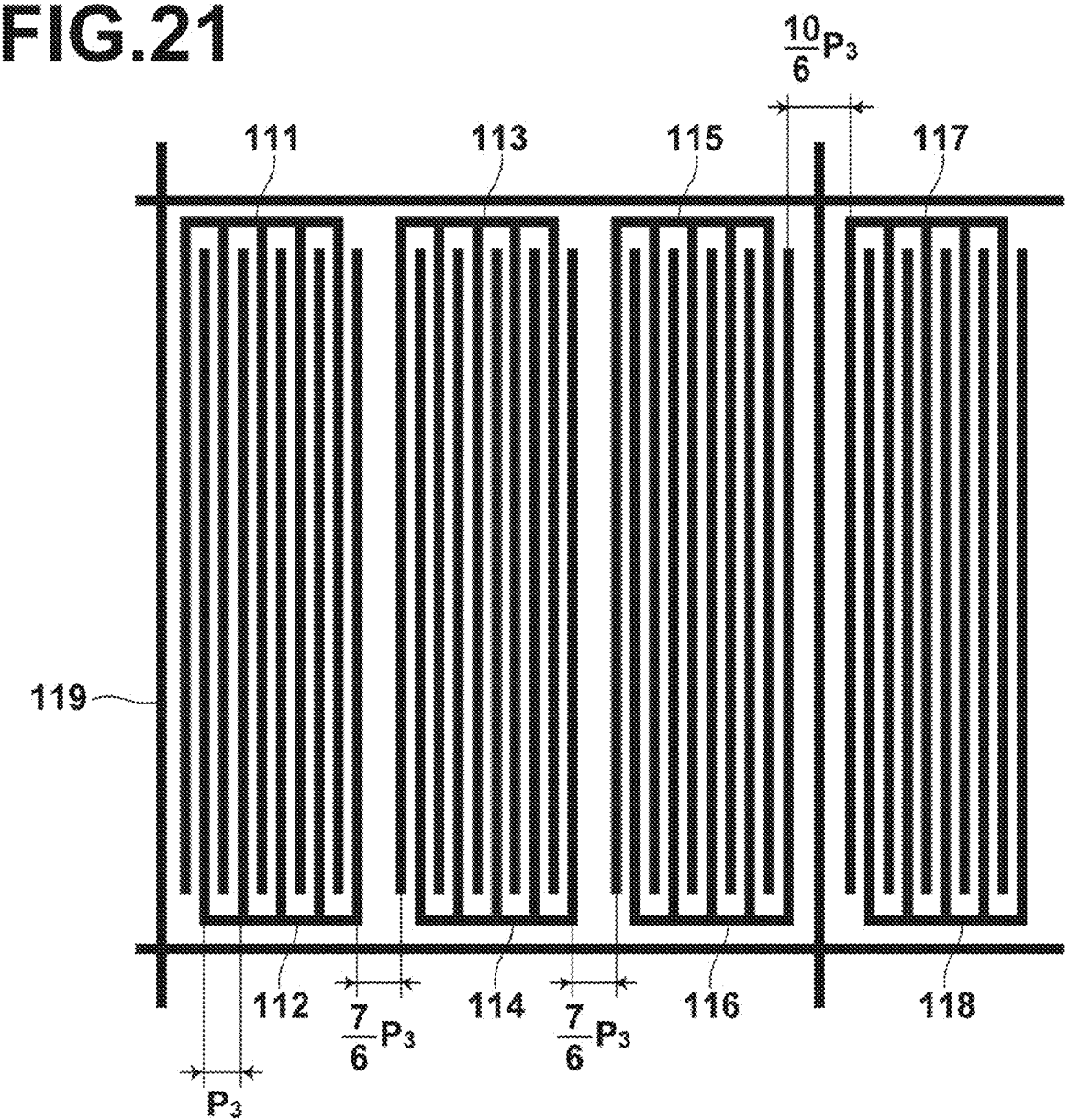
FIG. 21 illustrates a modification of the periodic information imaging radiation image detector of the radiation phase contrast imaging apparatus according to the second embodiment.

In addition to first to sixth linear electrode groups 111 to 116 shown in FIG. 20, constant potential electrode 119 may be provided in a grid pattern enclosing the charge collection electrode, constituted by first to sixth linear electrodes 111 to 116, of each unit element 72, as illustrated in FIG. 21. The effect of the constant potential electrode 119 is identical to that described in relation to FIG. 18. A potential that does not cause a large potential difference with an adjacent charge collection electrode is applied to constant potential electrode 119. That is, substantially the same potential as that of the charge collection electrode is applied. More specifically, constant potential electrode 119 is set to a ground potential or a value close to the ground potential. Where constant potential electrode 119 is provided, the pitch between linear electrode groups of adjacent pixels in a direction orthogonal to the linear electrodes, i.e., between linear electrode group 116 and linear electrode group 117, is set to $(10/6) \times P_3$, as shown in FIG. 21.

Figure 22:
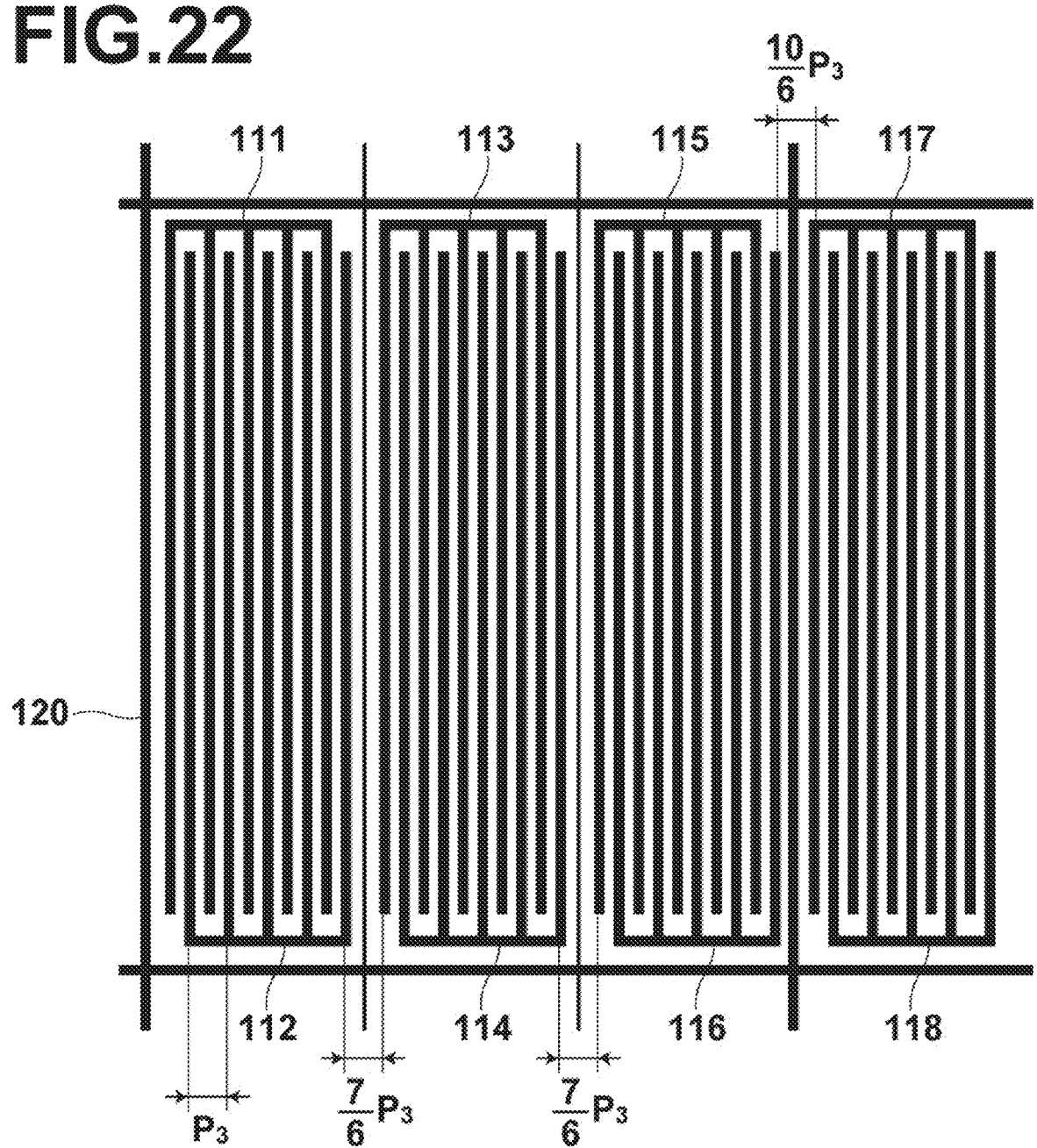
FIG. 22 illustrates a modification of the periodic information imaging radiation image detector of the radiation phase contrast imaging apparatus according to the second embodiment.

Instead of providing constant potential electrode 119 to enclose each pixel, as shown in FIG. 21, constant potential electrode 120 may be provided to enclose each sub-pixel, as shown in FIG. 22.

Figure 23:
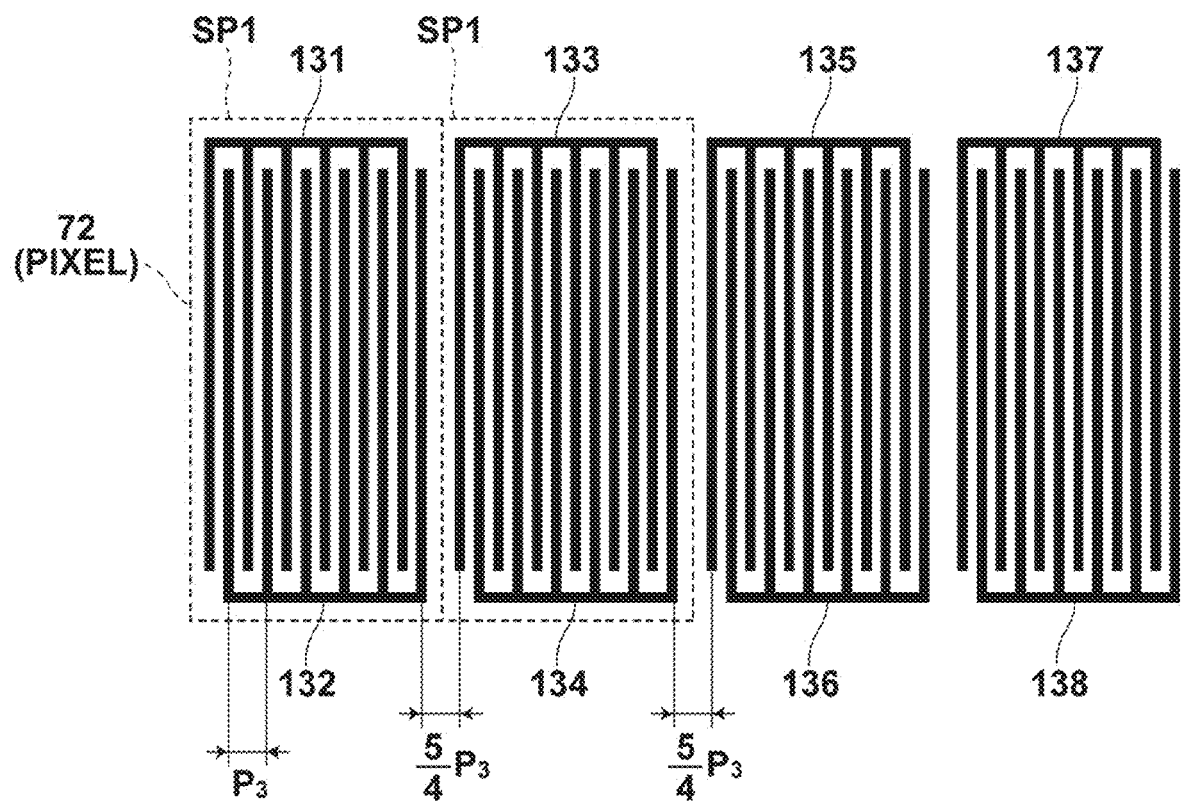
FIG. 23 illustrates a modification of the periodic information imaging radiation image detector of the radiation phase contrast imaging apparatus according to the second embodiment.

Further, as illustrated in FIG. 23, a pixel corresponding to one unit element 72 may be divided into two sub-pixels, and linear electrode groups having different phases may be disposed in each sub-pixel. More specifically, in the modification shown in FIG. 23, first linear electrode group 131 in which linear electrodes are arranged with pitch $P_3$ and second linear electrode group 132 in which linear electrodes are arranged with pitch $P_3$ are disposed in sub-pixel SP1 so as to have a phase difference of π from each other, third linear electrode group 133 in which linear electrodes are arranged with pitch $P_3$ and fourth linear electrode group 134 in which linear electrodes are arranged with pitch $P_3$ are disposed in sub-pixel SP2 so as to have a phase difference of π from each other. Then, adjacent linear electrode groups of sub-pixel SP1 and sub-pixel SP2 are disposed at a distance of $(5/4) \times P_3$. This arrangement results in that, when the phase of first linear electrode group 131 is assumed to be 0, the phase of second linear electrode group 132 is π, the phase of third linear electrode group 133 is $3\pi/2$, the phase of fourth linear electrode group 134 is $\pi/2$, that is, first to fourth linear electrode groups correspond to the phases shifted by $\pi/2$ from each other. Linear electrode groups 135 to 138 are linear electrode groups of adjacent pixel. Linear electrode group 135 detects a signal having the same phase as that of first linear electrode group 131, linear electrode group 136 detects a signal having the same phase as that of second linear electrode group 132, linear electrode group 137 detects a signal having the same phase as that of third linear electrode group 133, and linear electrode group 138 detects a signal having the same phase as that of fourth linear electrode group 134.

Formation of the charge collection electrode in the manner illustrated in FIG. 23 to read out charges collected by first to fourth linear electrode groups 131 to 134 with respect to each linear electrode group allows acquisition of image signals corresponding to four types of phase components by one image acquiring operation.

FIG. 20 or 23 illustrates a case where a pixel corresponding to one unit element 72 is divided into three or two sub-pixels, but the pixel may be divided into n ($n \geq 4$) sub-pixels. In this case, if the pitch between adjacent linear electrode groups of adjacent sub-pixels is set to $(2n+1)P_3/2n$, linear electrode groups corresponding to phases shifted by $\pi/n$ from each other may be provided.

When a pixel is divided into two to three sub-pixels, data of four to six phase components may be obtained by one image acquiring operation, and a preferable phase image may be formed. When obtaining data of four to six phase components without dividing a pixel into sub-pixels, the structure shown in FIG. 19 may be used, but each linear electrode has a narrow width, which may cause a manufacturing problem. On the other hand, $n \geq 4$ while maintaining the pixel size causes each linear electrode group to have a less number of linear electrodes, whereby the accuracy as the data of phase components is degraded.

When diving a pixel into a plurality of sub-pixels in the manner as described above, it is preferable to set the width of the pair of linear electrode groups in the length direction of the linear electrodes in each sub-pixel greater than the width of the pair of linear electrode groups in a direction orthogonal to the length direction of the linear electrodes, as illustrated in FIGS. 20 to 22.

Figure 24:
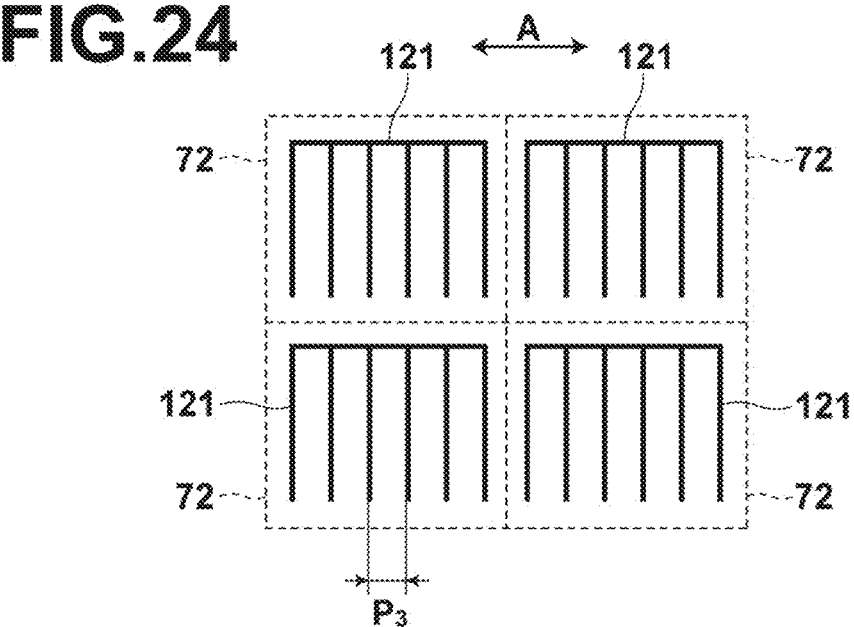
FIG. 24 illustrates a modification of the periodic information imaging radiation image detector of the radiation phase contrast imaging apparatus according to the second embodiment.

The modification described above is an example in which a plurality of linear electrode groups is provided in each unit element 72. But, for example, only one linear electrode group 121, in which linear electrodes are arranged with pitch $P_3$, may be provided in each unit element 72, as illustrated in FIG. 24. FIG. 24 illustrates linear electrode groups 121 of four adjacent unit elements 72. As illustrated in FIG. 24, where the charge collection electrode of unit element 72 is formed of one linear electrode group and image signals corresponding to a plurality of types of phase components having different phases are obtained, a shifting mechanism for shifting periodic information imaging radiation image detector 40 and grating 20 in a direction orthogonal to linear electrodes (arrow A direction in FIG. 24) along the respective planes may be provided and radiation image taking may be performed a plurality of times by shifting detector 40 and grating 20. For example, image signals corresponding to three types of phase components may be obtained by shifting detector 40 and grating 20 by ⅓ of pitch $P_3$ and taking a radiation image at each position. Otherwise, image signals corresponding to six types of phase components may be obtained by shifting detector 40 and grating 20 by ⅙ of pitch $P_3$ and taking a radiation image at each position.

In addition to the charge collection electrodes of linear electrode groups 121 shown in FIG. 24, constant potential electrode 122 may be provided as illustrated in FIG. 25. Constant potential electrode 122 is arranged so as to be disposed between each linear electrode of each linear electrode group 121 and in a grid pattern to enclose each unit element 72. The effect of the constant potential electrode 122 is identical to that described in relation to FIG. 18. A potential that does not cause a large potential difference with an adjacent charge collection electrode is applied to constant potential electrode 122. That is, substantially the same potential as that of the charge collection electrode is applied. More specifically, constant potential electrode 122 is set to a ground potential or a value close to the ground potential.

In FIG. 16, the description has been made of a case in which first linear electrode group 81a and second linear electrode group 81b are phase shifted by $\pi$ from each other, but instead, three linear electrode groups phase shifted by $2\pi/3$ from each other may be provided in each unit element 72. If the charge collection electrode of each unit element 72 is formed of three linear electrode groups in the manner as described above and periodic information imaging radiation image detector 40 and grating 20 are shifted, for example, by ½ of pitch $P_3$ to take a radiation image at each position, image signals corresponding to six types of phase components may be obtained.

The radiation phase contrast imaging apparatus according to the second embodiment uses a radiation image detector having TFT switches, but a CMOS or a CCD may also be used as the switch element.

Further, in the radiation phase contrast imaging apparatus according to the second embodiment, periodic information imaging radiation image detector 40 to which a positive voltage is applied when recording a radiation image is used. Alternatively, a TFT readout type radiation image detector to which a negative voltage is applied when recording a radiation image may be used.

Figure 26A:
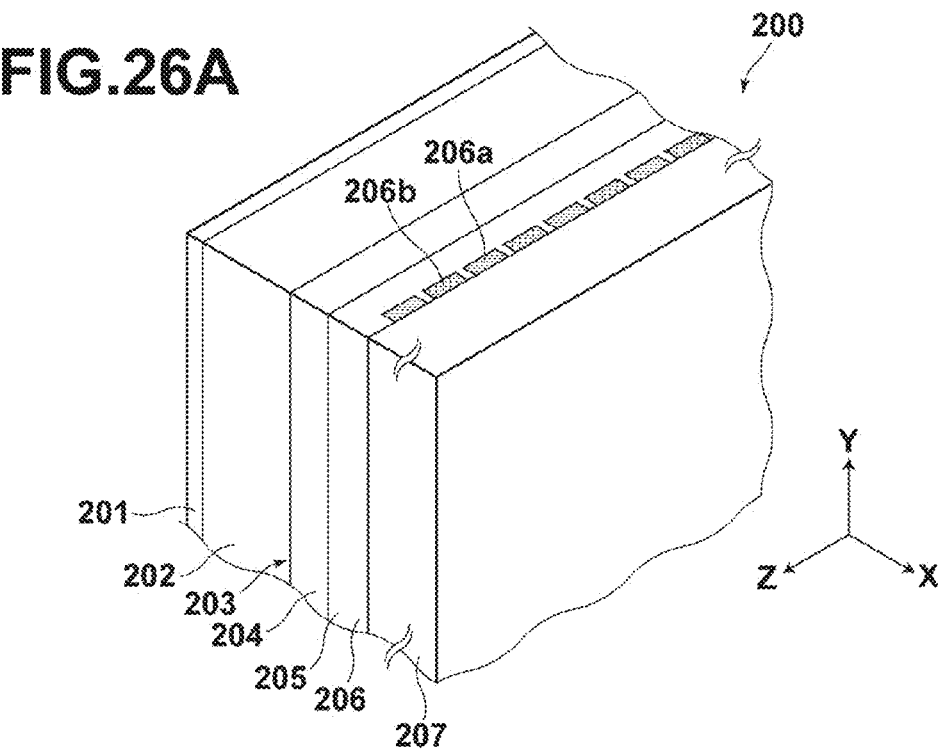
FIG. 26A is a cross-sectional view of a periodic information imaging radiation image detector of the radiation phase contrast imaging apparatus according to the third embodiment, illustrating the schematic construction thereof.

Next, a third embodiment of the radiation phase contrast imaging apparatus of the present invention will be described. The radiation phase contrast imaging apparatus according to the third embodiment uses an optical readout type periodic information imaging radiation image detector, instead of the TFT readout type periodic information imaging radiation image detector of the radiation phase contrast imaging apparatus according to the second embodiment. The radiation phase contrast imaging apparatus according to the third embodiment differs from the radiation phase contrast imaging apparatus according to the second embodiment only in the structure of the periodic information imaging radiation image detector. Accordingly, only the structure of the periodic information imaging radiation image detector will be described. FIG. 26A is a perspective view of the periodic information imaging radiation image detector, FIG. 26B is an XZ cross-sectional view of the periodic information imaging radiation image detector shown in FIG. 26A, and FIG. 26C is an XY cross-sectional view of the periodic information imaging radiation image detector shown in FIG. 26A.

Figure 26B:
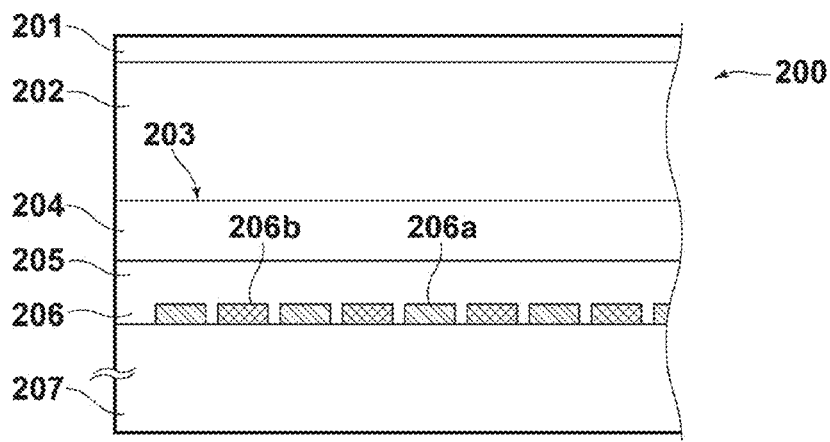
FIG. 26B is an XZ sectional view of the periodic information imaging radiation image detector shown in FIG. 26A.
Figure 26C:
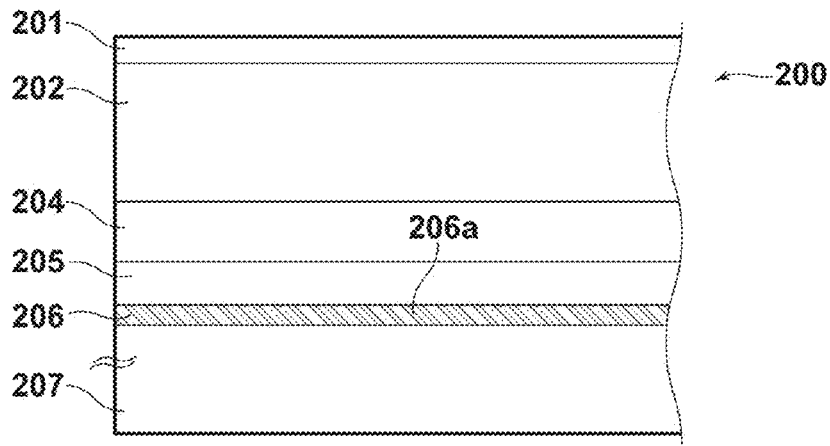
FIG. 26C is an XY sectional view of the periodic information imaging radiation image detector shown in FIG. 26A.

As illustrated in FIGS. 26A to 26C, periodic information imaging radiation image detector 200 of the radiation phase contrast imaging apparatus according to the third embodiment includes the following stacked in the order listed below: first electrode layer 201 that transmits radiation; recording photoconductive layer 202 that generates charges by receiving radiation transmitted through first electrode layer 201; charge transport layer 204 that acts as an insulator against charges of one polarity of those generated in recording photoconductive layer 202 and as a conductor for charges of the other polarity; readout photoconductive layer 205 that generates charges by receiving readout light; and second electrode layer 206. Storage section 203 for storing charges generated in recording photoconductive layer 202 is formed adjacent to the interface between recording photoconductive layer 202 and charge transport layer 204. Each of the layers described above is stacked on glass substrate 207 one after another from second electrode layer 206.

As for first electrode layer 201, any material may be used as long as it transmits radiation. For example, a NESA film ($SnO_2$), ITO (Indium Tin Oxide), IZO (Indium Zinc Oxide) IDIXO (Idemitsu Indium X-metal Oxide: Idemitsu Kosan Co., Ltd), or the like with a thickness of 50 to 200 nm may be used. Alternatively, Al or Au with a thickness of 100 nm may be used.

Second electrode layer 206 includes a plurality of transparent linear electrodes 206a that transmits readout light and a plurality of opaque linear electrodes 206b that blocks the readout light. Transparent linear electrodes 206a and opaque linear electrodes 206b extend from one end of an image forming area of periodic information imaging radiation image detector 200 to the other end continuously and straightly. As illustrated in FIGS. 26A and 26B, transparent linear electrodes 206a and opaque linear electrodes 206b are disposed alternately in parallel at a predetermined distance.

Transparent linear electrodes 206a are formed of a material that transmits readout light and has conductivity. For example, ITO, IZO, or IDIXO may be used as in first electrode layer 201. The thickness of each electrode 206a is about 100 to 200 nm.

Opaque linear electrodes 206b are formed of a material that blocks the readout light and has conductivity. It is preferable that opaque linear electrodes 206b transmit erasure light, and a combination of one of the transparent conductive materials described above with a color filter is used as the opaque linear electrode 206b. The thickness of the transparent conductive material is about 100 to 200 nm.

As will be described later, an image signal is read out by adjacent transparent linear electrode 206a and opaque linear electrode 206b as a pair. In periodic information imaging radiation image detector 200 of the present embodiment, 20 pairs of transparent linear electrode 206a and opaque linear electrode 206b are disposed in the width of one pixel constituting a radiation image, as illustrated in FIG. 27. That is, 20 linear electrode pairs from first linear electrode pair 211, second linear electrode pair 212, third linear electrode pair 213, and so forth are disposed within the width of one pixel.

As illustrated in FIG. 27, the linear electrode pairs are disposed such that the distance between every other pairs, e.g., the distance between first linear electrode pair 211 and third linear electrode pair 213, or the distance between second linear electrode pair 212 and fourth linear electrode pair 214, corresponds to pitch $P_3$. Pitch $P_3$ is set to a value in the range from 2 to 15 μm. A first linear electrode group is formed of $(2n-1)^{th}$ (n is an integer not smaller than 1 and not greater than 10) linear electrode pair and a second linear electrode group is formed of $(2n)^{th}$ (n is an integer not smaller than 1 and not greater than 10) linear electrode pair.

Also in the present embodiment, the focus of radiation corresponding to each electron source 15a, grating 20, and periodic information imaging radiation image detector 200 are disposed at predetermined distances in the optical axis direction of the radiation, as in the radiation phase contrast imaging apparatus of the second embodiment.

More specifically, the radiation phase contrast imaging apparatus of the present embodiment is configured such that the interval $P_0$ between the center of each focus of radiation corresponding to each electron source 15a, the distance $L_2$ (FIG. 11) between the focus and grating 20, the distance $Z_2$ (FIG. 11) between grating 20 and periodic information imaging radiation image detector 200, and interval $P_3$ (FIG. 27) between linear electrodes constituting periodic information imaging radiation image detector 200 satisfy Formula (7) below.

$$P_0 = P_3 \times L_2/Z_2 \quad (7)$$

Then, the first and second linear electrode groups within the width of one pixel described above are alternately disposed repeatedly in the direction orthogonal to the length direction of the linear electrodes. In this case, first linear electrode groups and second linear electrode groups are disposed such that the phase of arrangement period of each linear electrode pair is shifted by $\pi$ from each other. Although not shown, transparent linear electrodes 206a of the first linear electrode groups are physically connected to each other with a connection wire, such as a lead wire. Also, transparent linear electrodes 206a of the second linear electrode groups are physically connected to each other with a connection wire, such as a lead wire.

Recording photoconductive layer 202 may be formed of any material as long as it generates charges when exposed to radiation. Here, a-Se based material having excellent properties, such as relatively high quantum efficiency to radiation and high dark resistance, is used. An appropriate layer thickness is in the range from 10 to 1500 µm. For a mammography application, in particular, a preferable layer thickness is in the range from 150 to 250 µm, and for a general radiography application, a preferable layer thickness is in the range from 500 to 1200 µm.

As for the material of charge transport layer 204, for example, a material having a greater difference in charge mobility between charges charged on first electrode layer 201 when a radiation image is recorded and the charges having opposite polarity (for example, not less than $10^2$, more preferably, not less than $10^3$), is preferably used. In this respect, organic compounds such as poly N-vinylcarbazole (PVK), N,N'-diphenyl-N,N'-bis(3-methylphenyl)-[1,1'-biphenyl]-4,4'-diamine (TPD), discotic liquid crystal, and the like, or semiconductor materials such as TPD-dispersed polymers (polycarbonate, polystyrene, PVK), a-Se doped with 10 to 200 ppm of Cl, $As_2Se_3$, and the like are preferably used. An appropriate thickness of charge transport layer is in the range from 0.2 to 2 µm.

Readout photoconductive layer 205 may be formed of any material as long as it shows conductivity when exposed to readout light. For example, a photoconductive material consisting primarily of at least one of a-Se, Se—Te, Se—As—Te, non-metal phthalocyanine, metal phthalocyanine, MgPc (magnesium phthalocyanine) VoPc (phase II of Vanadyl phthalocyanine, CuPc (copper phthalocyanine), and the like is preferably used. An appropriate thickness of photoconductive layer 205 is in the range from 5 to 20 µm.

Next, an operation of the radiation phase contrast imaging apparatus according to the third embodiment for recording a radiation image to and reading out from the periodic information imaging radiation image detector will be described.

The operation steps from the emission of radiation from radiation emission unit 1 to the formation of a self-image by grating 20 are identical to those of the radiation phase contrast imaging apparatus according to the second embodiment, and therefore will not be elaborated upon further here.

Figure 28A:
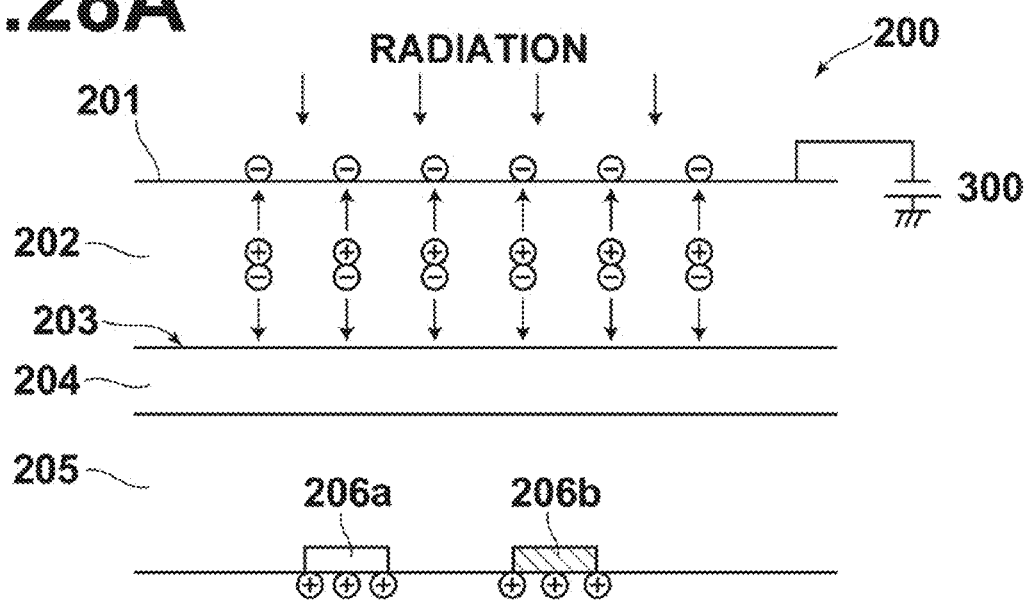
FIGS. 28A, 28B illustrate a recording operation for recording a radiation image in the periodic information imaging radiation image detector in the third embodiment of the radiation phase contrast imaging apparatus of the present invention.

Thereafter, as illustrated in FIG. 28A, with a negative voltage being applied to first electrode layer 201 of periodic information imaging radiation image detector 200 by high voltage source 300, radiation representing a self-image of grating 20 formed by grating 20 is emitted to periodic information imaging radiation image detector 200 from the side of first electrode layer 201.

Figure 28B:
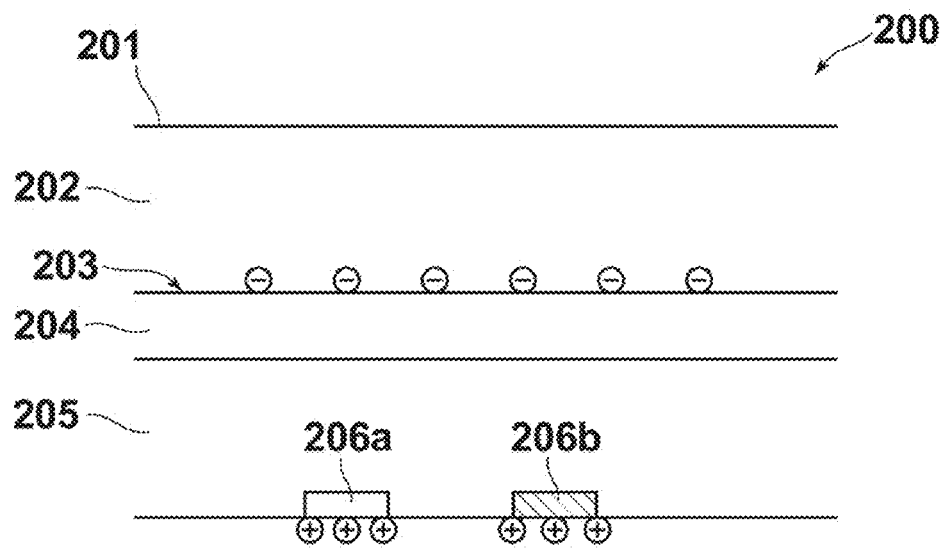

The radiation emitted onto periodic information imaging radiation image detector 200 transmits through first electrode layer 201 and reaches recording photoconductive layer 202. Then, recording photoconductive layer 202 generates charge pairs by the exposure of the radiation, and positive charges of the charge pairs are combined with negative charges charged on the first electrode layer 201 and dissolved, while negative charges of the charge pairs are stored, as latent image charges, in storage section 203 formed at the interface between recording photoconductive layer 202 and charge transport layer 204 (FIG. 28B).

Here, in periodic information imaging radiation image detector 200 of radiation phase contrast imaging apparatus of the present embodiment, second electrode layer 206 for collecting charges generated in recording photoconductive layer 202 to storage section 203 is constituted by transparent linear electrode 206a and opaque linear electrode 206b. Therefore, when a voltage is applied to first electrode layer 201 in the manner as described above, electric fields are formed in recording photoconductive layer 202 from transparent linear electrode 206a and opaque linear electrode 206b toward first electrode layer 201 substantially parallel to each other, i.e., substantially perpendicular to the surface of first electrode layer 201. Negative charges generated in recording photoconductive layer 202 are moved toward each linear electrode along the electric field without spreading and collected in storage section 203, so that transparent linear electrode 206a and opaque linear electrode 206b perform a function equivalent to that of the combination of an amplitude diffraction grating and a detector provided in the later stage of the grating. Accordingly, charges representing an intensity modified signal through superimposition of the deformed self-image of grating 20 with a virtual grating formed by the first linear electrode group constituted by $(2n-1)^{th}$ (n is an integer not smaller than 1 and not greater than 10) linear electrode pairs shown in FIG. 27 are stored in a portion of storage section 203 above the first linear electrode group, and charges representing an intensity modified signal through superimposition of the deformed self-image of grating 20 with a virtual grating formed by the second linear electrode group constituted by $(2n)^{th}$ (n is an integer not smaller than 1 and not greater than 10) linear electrode pairs shown in FIG. 27 are stored in a portion of storage section 203 above the second linear electrode group. As described above, the first linear electrode group and second linear electrode group are phase shifted by $\pi$ from each other, so that signals corresponding to two types of phase components phase shifted from each other by $\pi$ are recorded in periodic information imaging radiation image detector 200.

Figure 29:
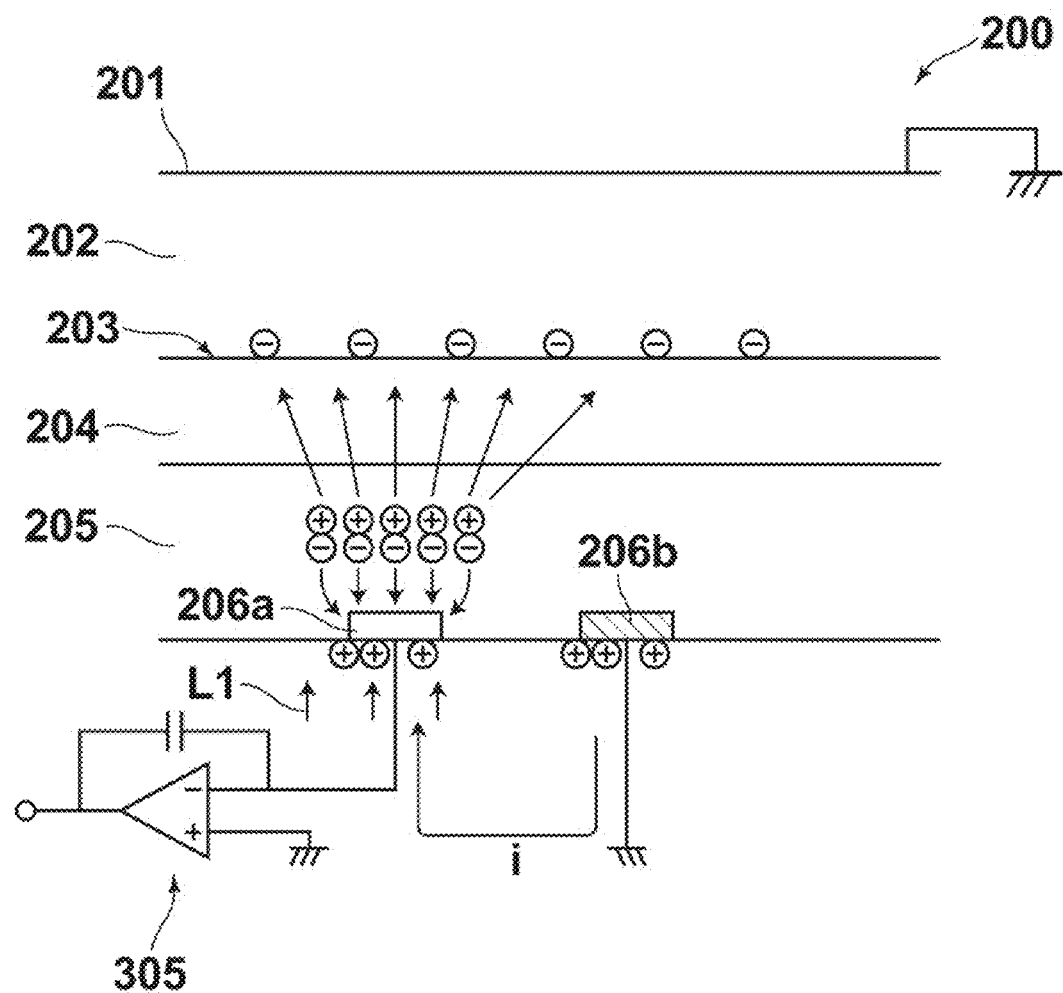
FIG. 29 illustrates a reading operation for reading out a radiation image from the periodic information imaging radiation image detector in the third embodiment of the radiation phase contrast imaging apparatus of the present invention.

Then, with the first electrode layer 201 being grounded, readout light L1 is emitted from the side of second linear electrode layer 206, as illustrated in FIG. 29. Readout light L1 transmits through transparent linear electrodes 206a and reaches readout photoconductive layer 205. Positive charges generated by the readout light L1 in readout photoconductive layer 205 combine with latent image charges in storage section 203 while negative charges combine with positive charges charged on opaque linear electrode 206b through charge amplifier 305 connected to opaque linear electrode 206b.

A current flows through charge amplifier 305 when the negative charges generated in readout photoconductive layer 205 are combined with the positive charges charged on opaque linear electrode 206b, and the current is integrated and detected as an image signal.

At this time, charges, flowed out from the first linear electrode group of first linear electrode pair 211 and third linear electrode pair 213 shown in FIG. 27, are detected by charge amplifier 305 as an image signal corresponding to a first phase component. In the mean time, charges, flowed out from the second linear electrode group of second linear electrode pair 212 and fourth linear electrode pair 214 shown in FIG. 27, are detected by charge amplifier 305 as an image signal corresponding to a second phase component.

Thereafter, periodic information imaging radiation image detector 200 is shifted by shifting mechanism 55, and the image recording in the detector 200 and image signal reading from the detector 200 are performed at each predetermined position, whereby image signals corresponding to the first and second phase components are detected at each predetermined position.

Image signals detected in the manner as described above are inputted to phase image acquisition unit 6. Then, phase image acquisition unit 6 generates a phase image based on image signals of a plurality of phase components.

For example, in the radiation phase contrast imaging apparatus of the third embodiment, image signals corresponding to six types of phase components may be obtained by shifting detector 200 and grating 20 by ⅓ of pitch $P_3$ in a direction orthogonal to the linear electrodes along the respective planes and taking a radiation image at each position.

Also, in the radiation phase contrast imaging apparatus of the third embodiment, linear electrode group pairs, in which respective linear electrode groups are disposed in order, may be disposed to different positions so as to have different phases as in the periodic information imaging radiation image detector of second embodiment. This allows image signals corresponding to sufficient number of phase components for forming a phase image to be obtained at the same time without requiring the shifting mechanism.

In the radiation phase contrast imaging apparatus of the third embodiment, periodic information imaging radiation image detector 200 to which a negative voltage is applied when recording a radiation image is used. Alternatively, an optical readout type periodic information imaging radiation image detector to which a positive voltage is applied when recording a radiation image may be used.

In the radiation phase contrast imaging apparatus according to the second or third embodiment, the description has been made of a case in which subject 10 is placed between radiation emission unit 1 and grating 20. When subject 10 is placed between grating 20 and periodic information imaging radiation image detector 40 or 200, the self-image of grating 20 produced at the position of periodic information imaging radiation image detector 40 or 200 is also deformed by subject 10. Therefore, also in this case, an image signal of a phase component modulated by subject 10 can be detected by periodic information imaging radiation image detector 40 or 200.

That is, in the radiation phase contrast imaging apparatus according to the second or third embodiment, subject 10 may be placed between radiation emission unit 1 and grating 20 or between grating 20 and periodic information imaging radiation image detector 40 or 200.

What is claimed is:

1. A radiation phase contrast imaging apparatus, comprising:
    a radiation emission unit having a plurality of electron sources, each for emitting an electron beam, and a target for emitting radiation through collision of the electron beam emitted from each electron source;
    a first grating in which grating structures for diffracting radiation emitted from the radiation emission unit are disposed periodically;
    a second grating in which grating structures for transmitting and shielding radiation diffracted by the first grating are disposed periodically; and
    a radiation image detector for detecting radiation transmitted through the second grating, wherein:
    the first and second gratings are disposed in an optical axis direction of the radiation so as to be able to substantially superimpose each image of the first grating formed based on radiation corresponding to each electron source on a surface of the second grating; and
    the radiation corresponding to each electron source is radiation that forms each phase image of the same subject on the radiation image detector by way of the first and second gratings.

2. The radiation phase contrast imaging apparatus of claim 1, wherein the apparatus is configured such that an interval $P_0$ between the center of each focus of the radiation corresponding to each electron source, a distance $L_1$ between the focus and the first grating, a distance $Z_1$ between the first grating and the second grating, and a periodic interval $P_2$ between shielding members constituting the second grating and disposed periodically satisfy Formula below $$P_0 = P_2 \times L_1 / Z_1.$$

3. The radiation phase contrast imaging apparatus of claim 1, wherein an interval between the center of each focus of the radiation corresponding to each electron source in a direction orthogonal to an extending direction of shielding members constituting the first grating is 10 to 500 μm.

4. The radiation phase contrast imaging apparatus of claim 1, further comprising an electron beam emission control unit for independently controlling the emission of electron beam from each of the plurality of electron sources to the target.

5. The radiation phase contrast imaging apparatus of claim 4, wherein the electron beam emission control unit is a unit that controls the emission of electron beam to the target by switching a voltage applied to a gate electrode provided between the electron sources and the target and restricts the passage of the electron beam.

6. The radiation phase contrast imaging apparatus of claim 4, wherein the electron beam emission control unit is a unit that controls the emission of electron beam to the target by switching a potential difference between an extraction electrode, which is provided between the electron sources and the target, and each electron source.

7. The radiation phase contrast imaging apparatus of claim 4, wherein the electron beam emission control unit is a unit that controls a focus interval of the radiation by independently controlling the emission of electron beam from each of the plurality of electron sources to the target.

8. The radiation phase contrast imaging apparatus of claim 7, wherein the electron beam emission control unit is a unit that controls the focus interval of the radiation such that the contrast of a moiré fringe pattern in a radiation image detected by the radiation image detector without a subject being present becomes maximum.

9. The radiation phase contrast imaging apparatus of claim 1, wherein the first grating is a phase modulation grating and the second grating is an amplitude modulation grating.

10. The radiation phase contrast imaging apparatus of claim 1, wherein the first and second gratings are phase modulation gratings.

11. A radiation phase contrast imaging apparatus, comprising:
- a radiation emission unit having a plurality of electron sources, each for emitting an electron beam, and a target for emitting radiation through collision of the electron beam emitted from each electron source;
- a grating in which grating structures for diffracting radiation emitted from the radiation emission unit are disposed periodically; and
- a periodic information imaging radiation image detector for detecting periodic information of radiation diffracted by the grating, wherein:
- the grating and the periodic information imaging radiation image detector are disposed in an optical axis direction of the radiation so as to be able to substantially superimpose each image of the grating formed based on radiation corresponding to each electron source on a surface of the periodic information imaging radiation image detector; and
- the radiation corresponding to each electron source is radiation that forms each phase image of the same subject inside of the periodic information imaging radiation image detector by way of the grating and linear electrodes of the periodic information imaging radiation image detector.

12. The radiation phase contrast imaging apparatus of claim 11, wherein the apparatus is configured such that an interval $P_0$ between the center of each focus of the radiation corresponding to each electron source, a distance $L_2$ between the focus and the grating, a distance $Z_2$ between the grating and the periodic information imaging radiation image detector, and an interval $P_3$ between the linear electrodes constituting the periodic information imaging radiation image detector satisfy Formula below $$P_0 = P_3 \times L_2/Z_2.$$

13. The radiation phase contrast imaging apparatus of claim 11, wherein an interval between the center of each focus of the radiation corresponding to each electron source in a direction orthogonal to an extending direction of shielding members constituting the grating is 10 to 500 µm.

14. The radiation phase contrast imaging apparatus of claim 11, further comprising an electron beam emission control unit for independently controlling the emission of electron beam from each of the plurality of electron sources to the target.

15. The radiation phase contrast imaging apparatus of claim 14, wherein the electron beam emission control unit is a unit that controls the emission of electron beam to the target by switching a voltage applied to a gate electrode provided between the electron sources and the target and restricts the passage of the electron beam.

16. The radiation phase contrast imaging apparatus of claim 14, wherein the electron beam emission control unit is a unit that controls the emission of electron beam to the target by switching a potential difference between an extraction electrode, which is provided between the electron sources and the target, and each electron source.

17. The radiation phase contrast imaging apparatus of claim 14, wherein the electron beam emission control unit is a unit that controls a focus interval of the radiation by independently controlling the emission of electron beam from each of the plurality of electron sources to the target.

18. The radiation phase contrast imaging apparatus of claim 17, wherein the electron beam emission control unit is a unit that controls the focus interval of the radiation such that the contrast of a moiré fringe pattern in a radiation image detected by the periodic information imaging radiation image detector without a subject being present becomes maximum.

* * * * *